United States Patent [19]
Allison et al.

[11] Patent Number: 5,811,097
[45] Date of Patent: Sep. 22, 1998

[54] BLOCKADE OF T LYMPHOCYTE DOWN-REGULATION ASSOCIATED WITH CTLA-4 SIGNALING

[75] Inventors: James Patrick Allison, Berkeley; Dana R. Leach, Albany; Matthew F. Krummel, Berkeley, all of Calif.

[73] Assignee: The Regents of the University of California, Oakland, Calif.

[21] Appl. No.: 646,605

[22] Filed: May 8, 1996

Related U.S. Application Data

[63] Continuation-in-part of Ser. No. 566,853, Dec. 4, 1995, which is a continuation-in-part of Ser. No. 506,666, Jul. 25, 1995, abandoned.

[51] Int. Cl.[6] ............... C07K 16/28; C07K 14/725; A61K 39/395
[52] U.S. Cl. ............... 424/144.1; 424/133.1; 424/141.1; 424/143.1; 424/152.1; 424/154.1; 424/130.1; 424/135.1; 424/810; 514/2; 514/12; 514/885; 530/387.1; 530/387.3; 530/388.1; 530/388.22; 530/388.7
[58] Field of Search ............... 424/130.1, 133.1, 424/135.1, 139.1, 143.1, 144.1, 810; 530/387.1, 388.22, 388.7; 514/885

[56] References Cited

U.S. PATENT DOCUMENTS

| | | | |
|---|---|---|---|
| 556,763 | 9/1896 | Ochoa et al. | 435/7.23 |
| 5,434,131 | 7/1995 | Linsley et al. | 514/2 |

FOREIGN PATENT DOCUMENTS

| | | |
|---|---|---|
| 0 613 944 | 9/1994 | European Pat. Off. |
| 0 682 039 | 11/1995 | European Pat. Off. |
| 93/00431 | 1/1993 | WIPO |
| 95/01994 | 1/1995 | WIPO |
| 95/03408 | 2/1995 | WIPO |
| 95/05464 | 2/1995 | WIPO |
| 95/23859 | 9/1995 | WIPO |
| 95/24217 | 9/1995 | WIPO |
| 95/33770 | 12/1995 | WIPO |
| 95/34320 | 12/1995 | WIPO |
| 96/14865 | 5/1996 | WIPO |

OTHER PUBLICATIONS

Damle et al., "Costimulation of T Lymphocytes with Integrin Ligands Intercellular Adhesion Molecule–1 or Vascular Cell Adhesion Molecule–1 Induces Functional Expression of CTLA–4, A Second Receptor for B7," *Journal of Immunology* 152:2686–2697 (1994).

Lin et al., "Long–Term Acceptance of Major Histocompatibility Complex Mismatched Cardiac Allografts Induced by CTLA4lg Plus Donor–Specific Transfusion," *J. Exp. Med.* 178:1801–1806 (1993).

Turka et al., "T–Cell Activation by the CD28 Ligand B7 is Required for Cardiac Allograft Rejection in vivo," *Proc. Natl. Acad. Sci. USA* 89:11102–11105 (1992).

Linsley, P.S. and J.A. Ledbetter, "The Role of the CD28 Receptor During T Cell Responses to Antigen," *Ann. Rev. Immunol.* 11:191–212 (1993).

Wu et al., "CTLA–4–B7 Interaction is Sufficient to Costimulate T Cell Clonal Expansion," *J. Exp. Med.* 185(7):1327–1335 (1997).

Linsley, P.S., "Distinct Roles for CD28 and Cytotoxic Lymphocyte–Associated Molecule–4 Receptors During T Cell Activation," *J. Exp. Med.*, 182:289–292 (1995).

Walumas, TL et al Immunity 1:403–413, Aug. 1994.

Kearney ER et al J. Immunol 155:1032–1036 Aug. 1, 1995.

*Primary Examiner*—Toni R. Scheiner
*Assistant Examiner*—John Lucas
*Attorney, Agent, or Firm*—Flehr Hohbach Test Albritton & Herbert, LLP

[57] ABSTRACT

T cell activation in response to antigen is increased by the administration of binding agents that block CTLA-4 signaling. When CTLA-4 signaling is thus blocked, the T cell response to antigen is released from inhibition. Such an enhanced response is useful for the treatment of tumors, chronic viral infections, and as an adjuvant during immunization.

11 Claims, 13 Drawing Sheets

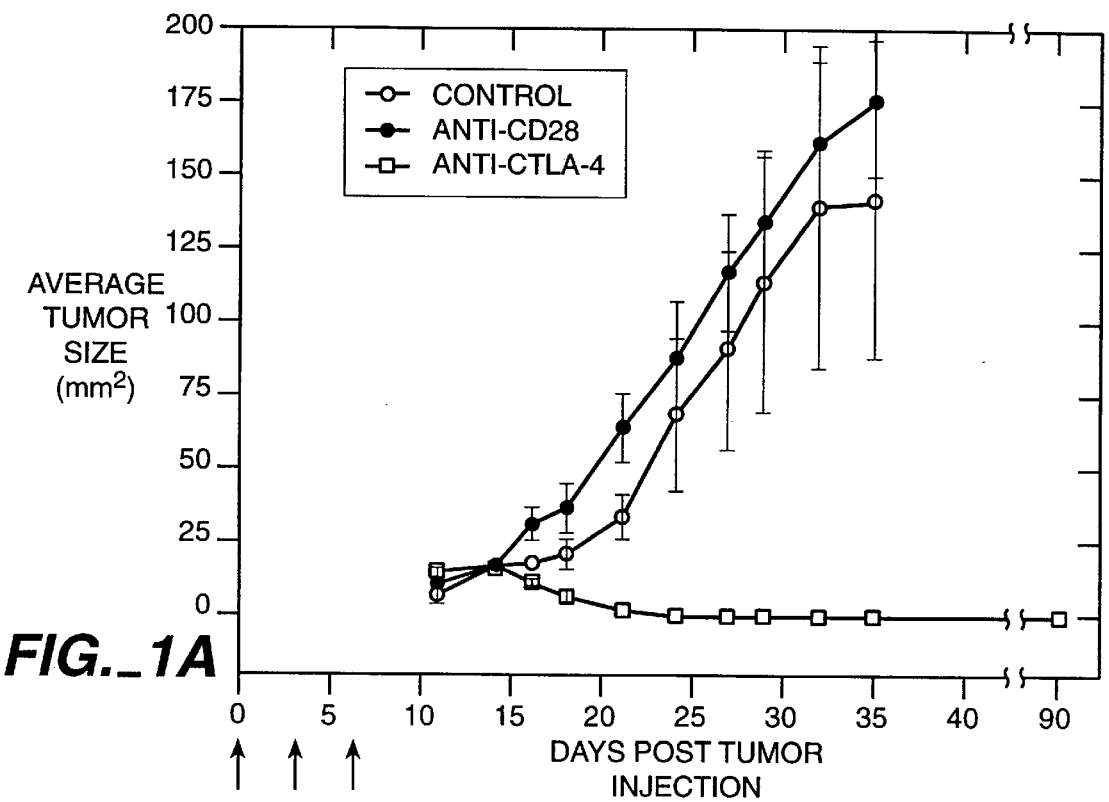
FIG._1A
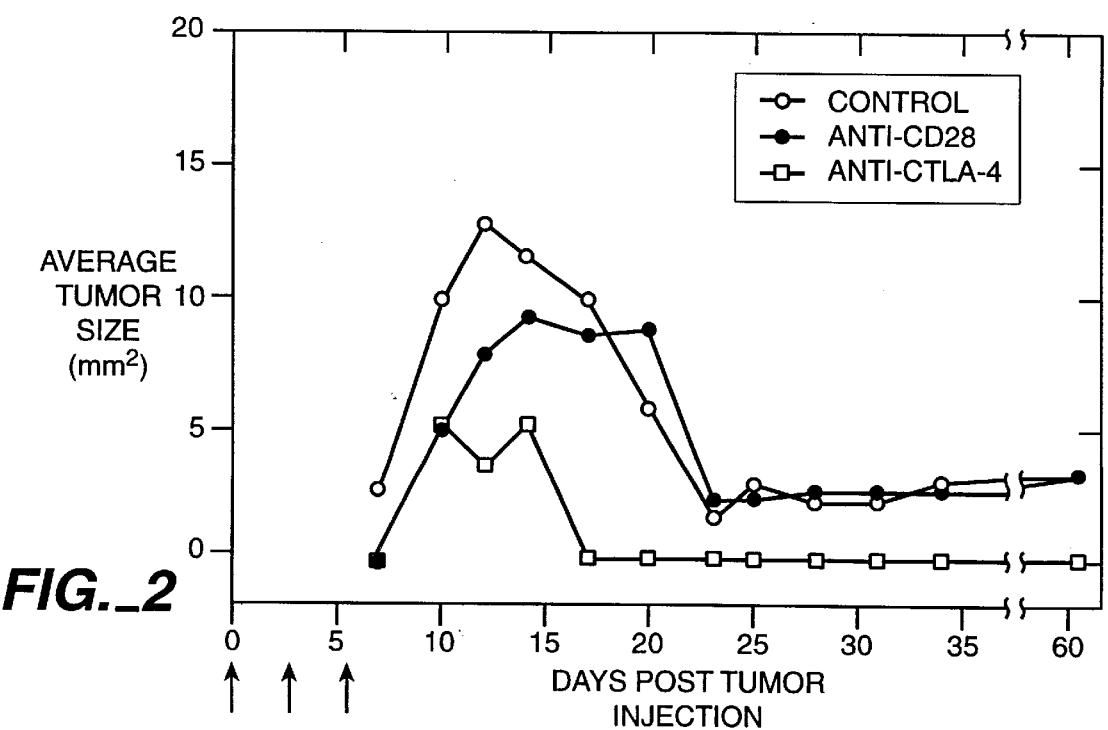
FIG._2

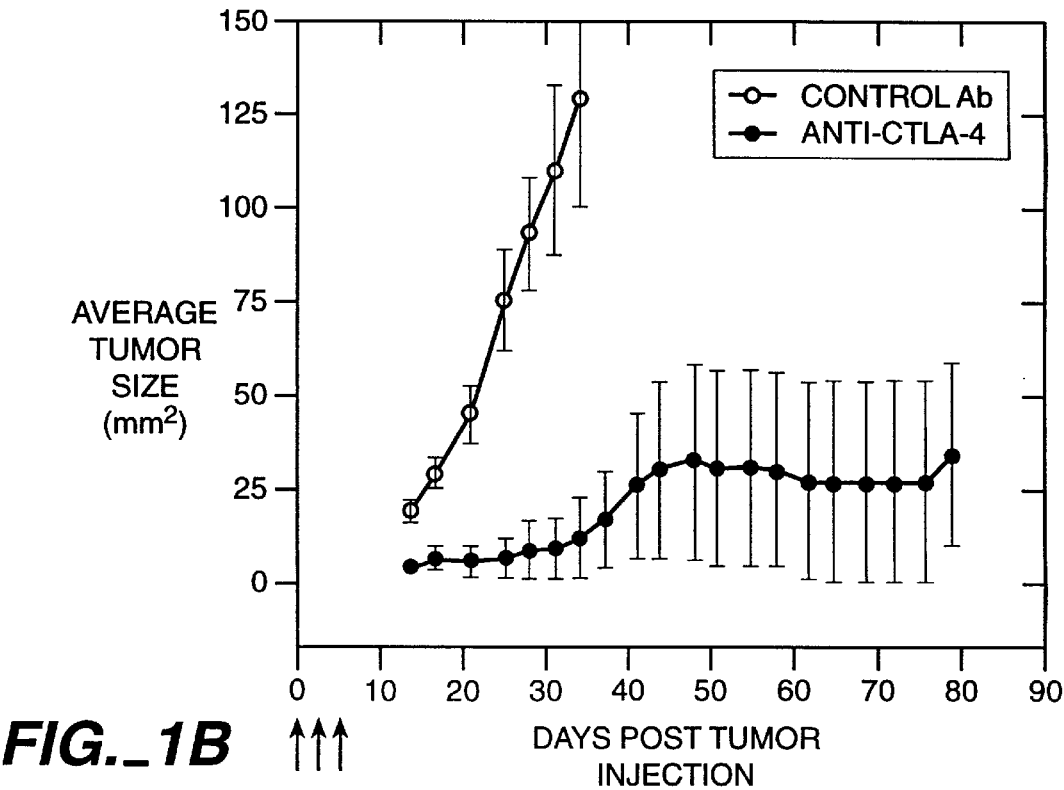
FIG._1B
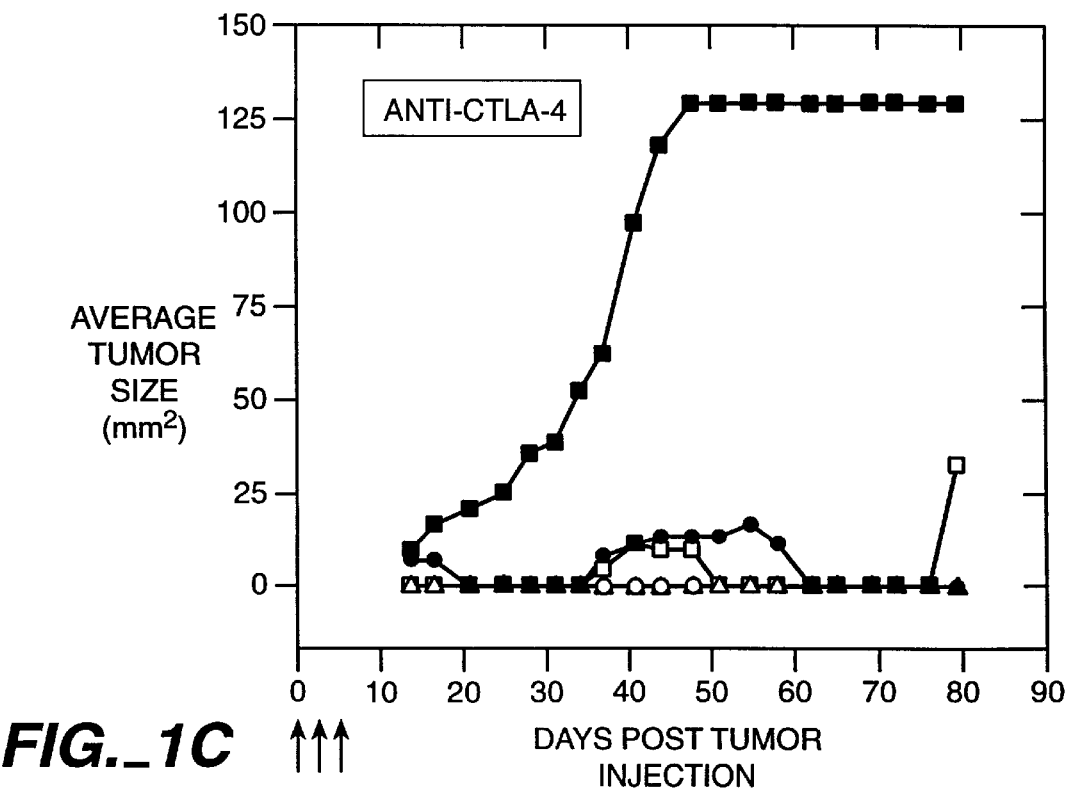
FIG._1C

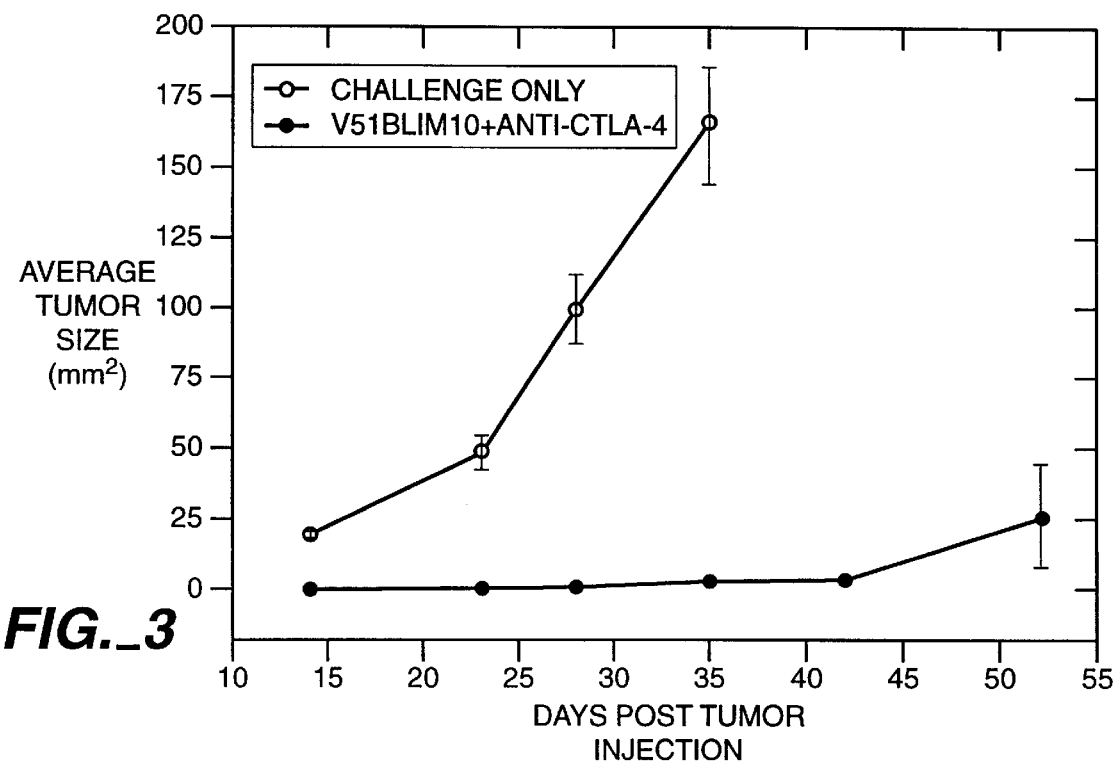
FIG._3
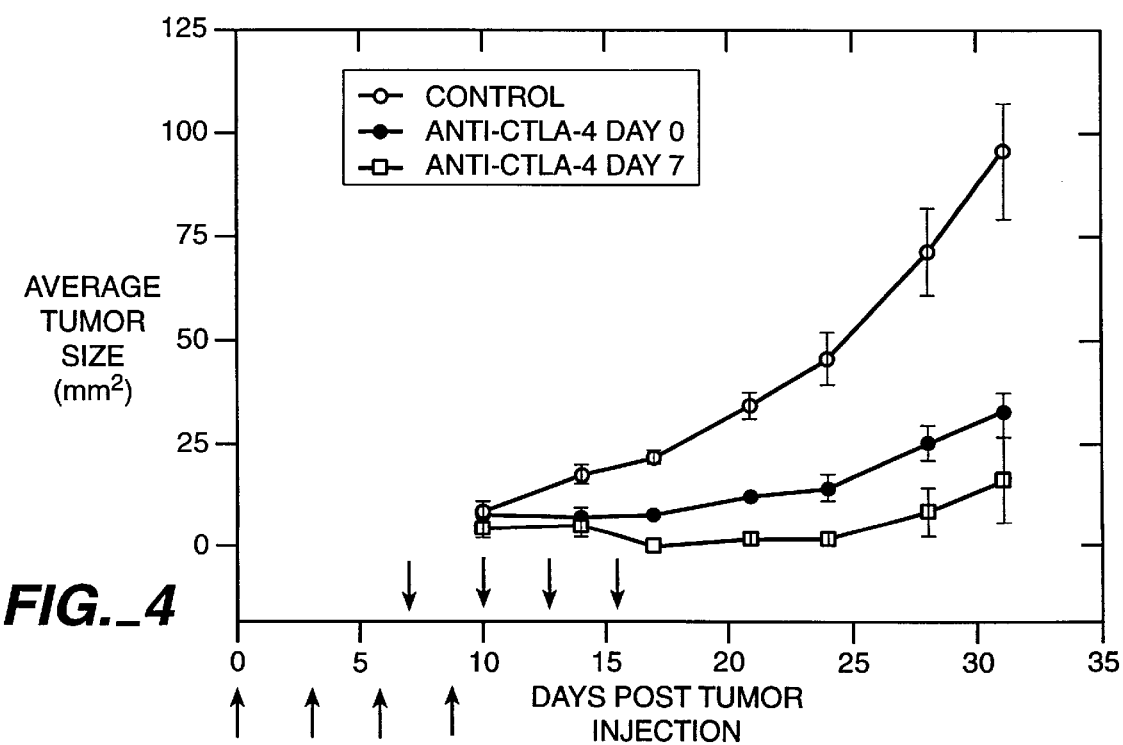
FIG._4

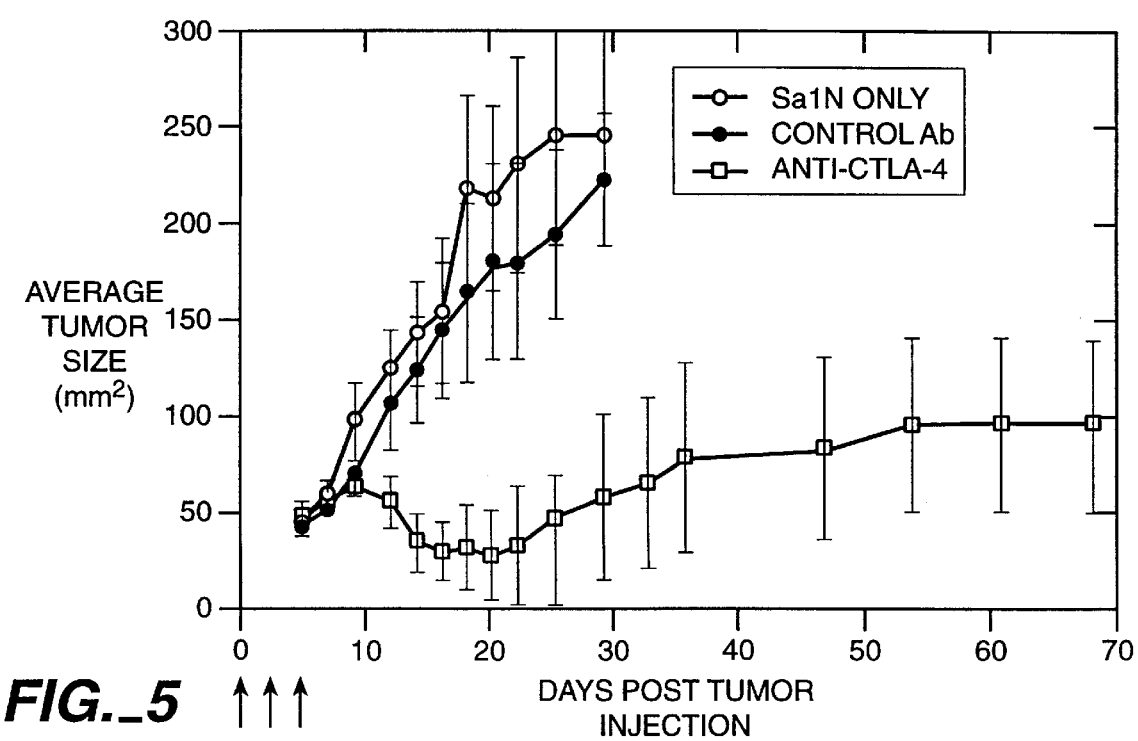
FIG._5

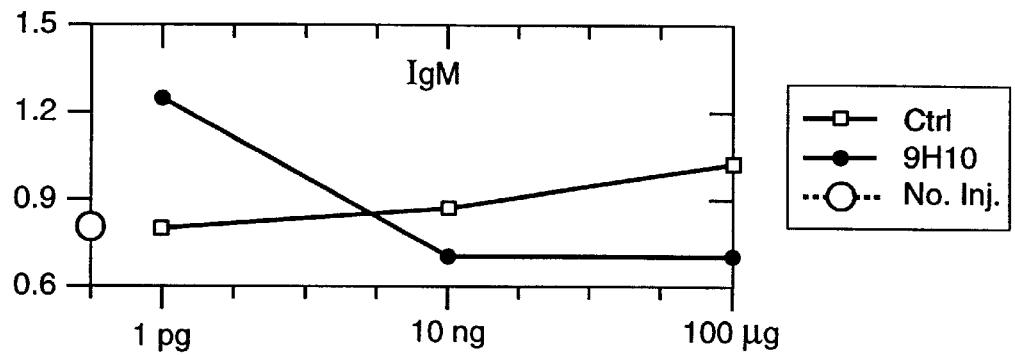
FIG._6A
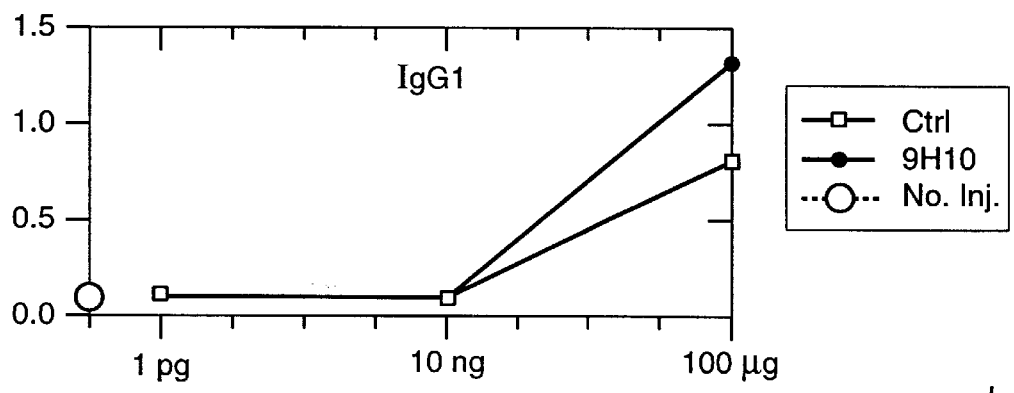
FIG._6B
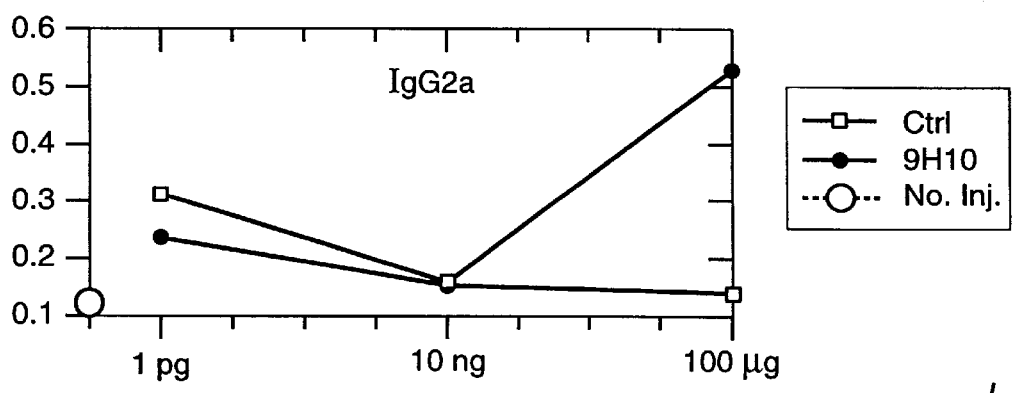
FIG._6C

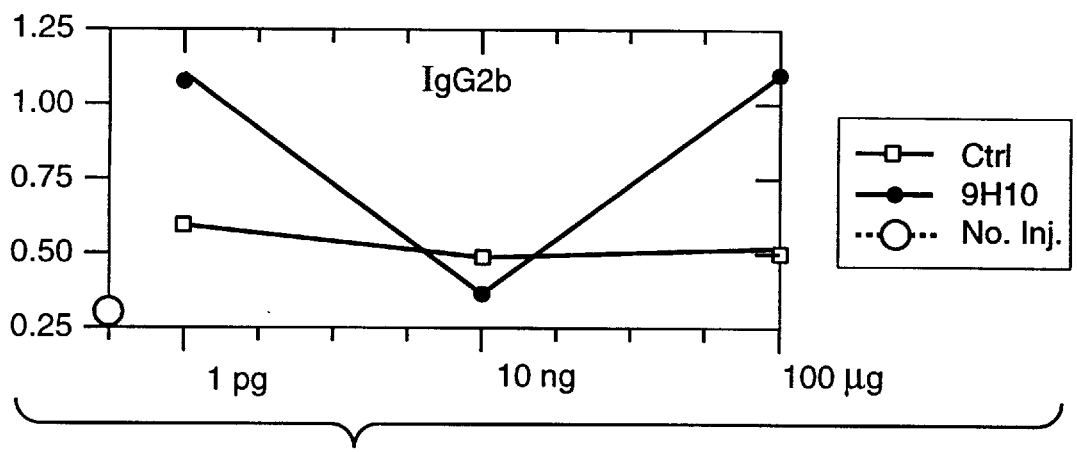
FIG._6D
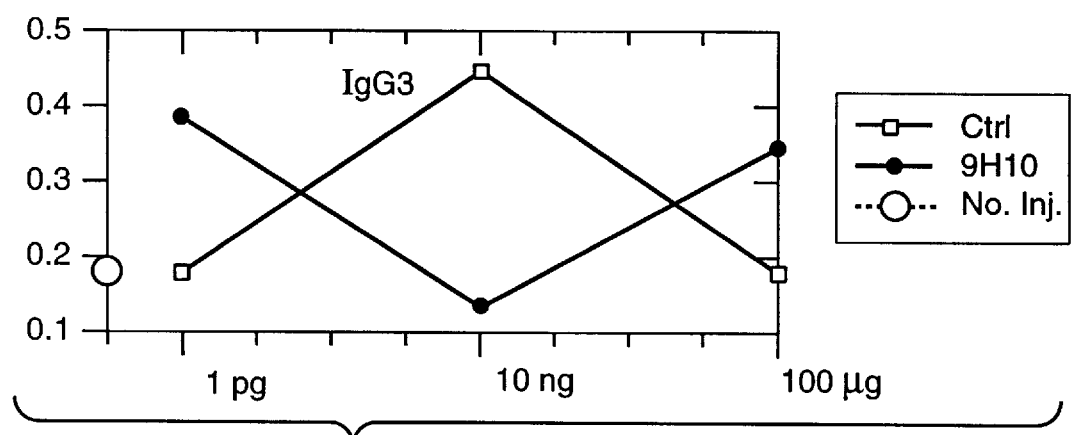
FIG._6E

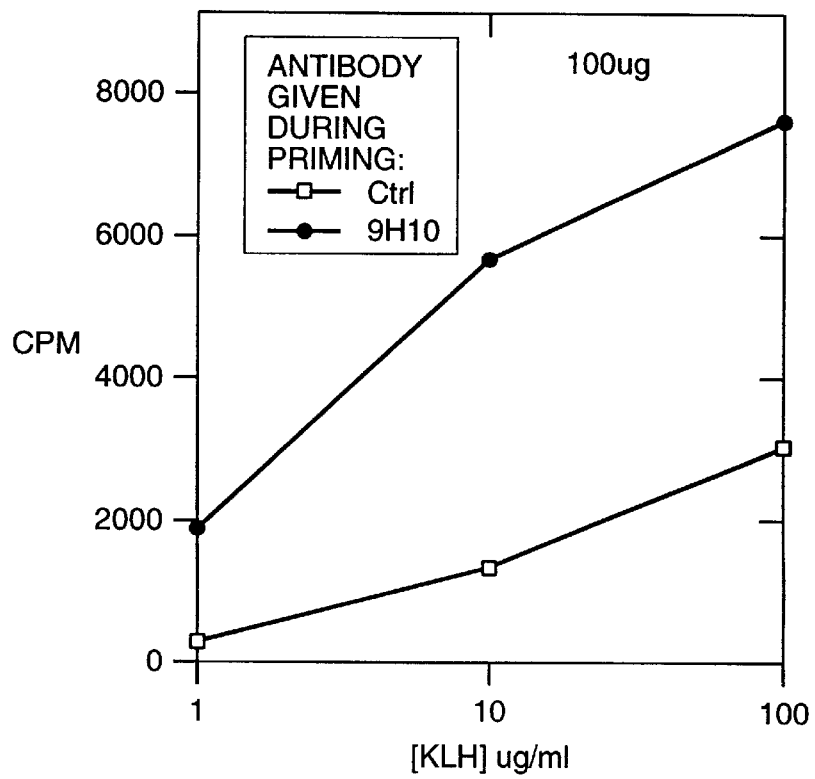
FIG._7A
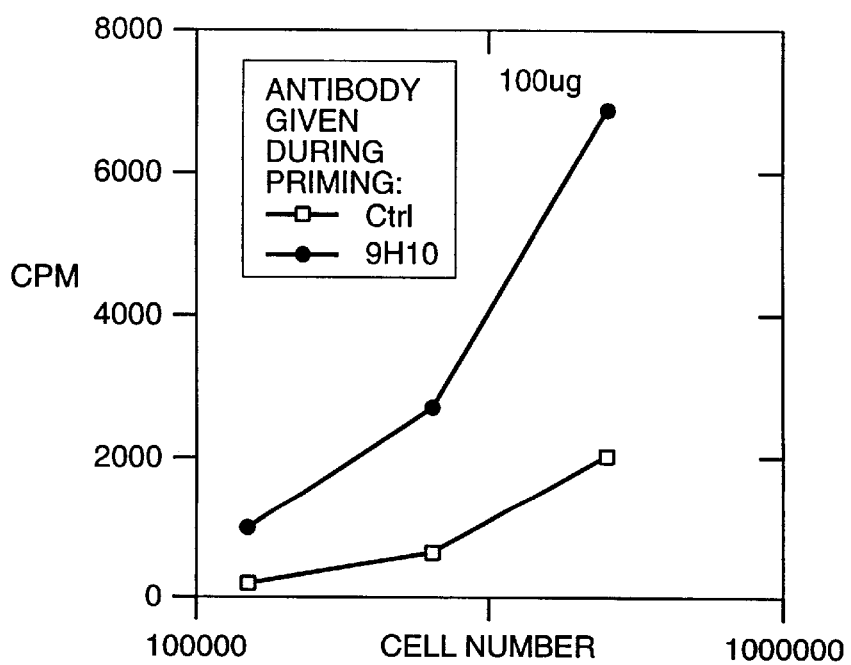
FIG._7B

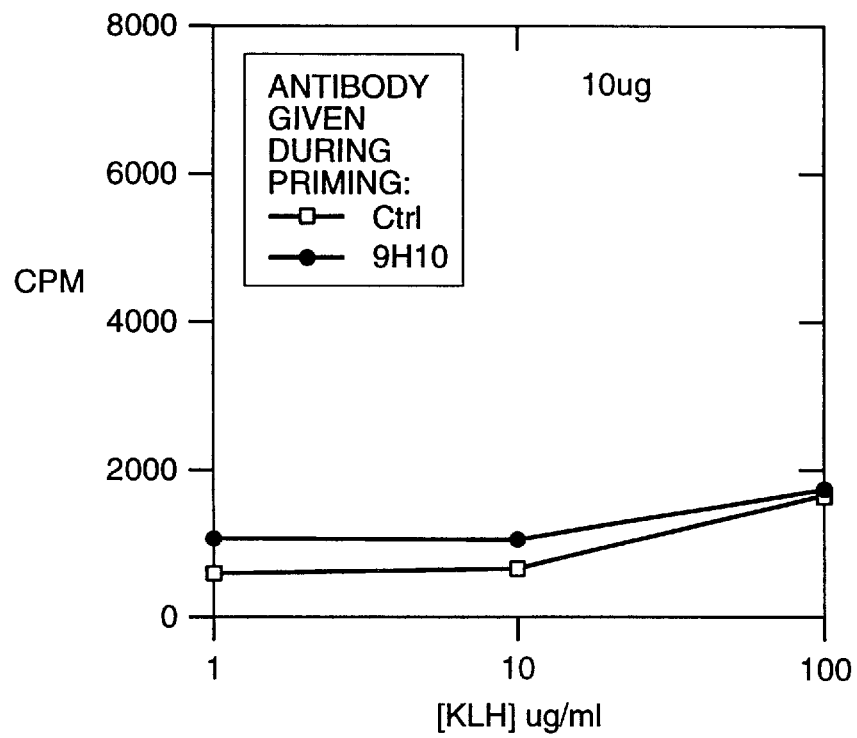
FIG._7C
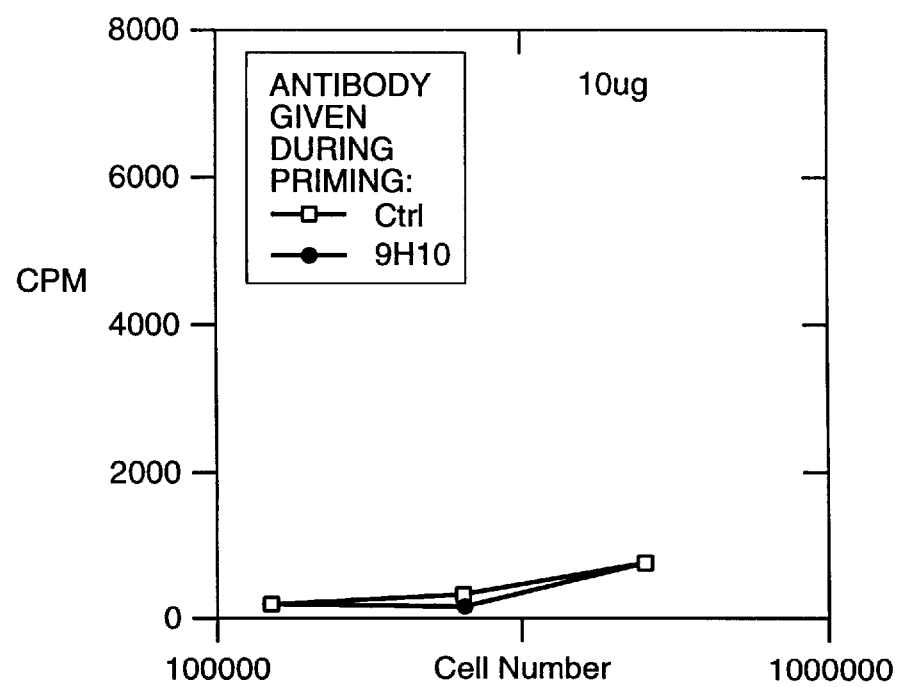
FIG._7D

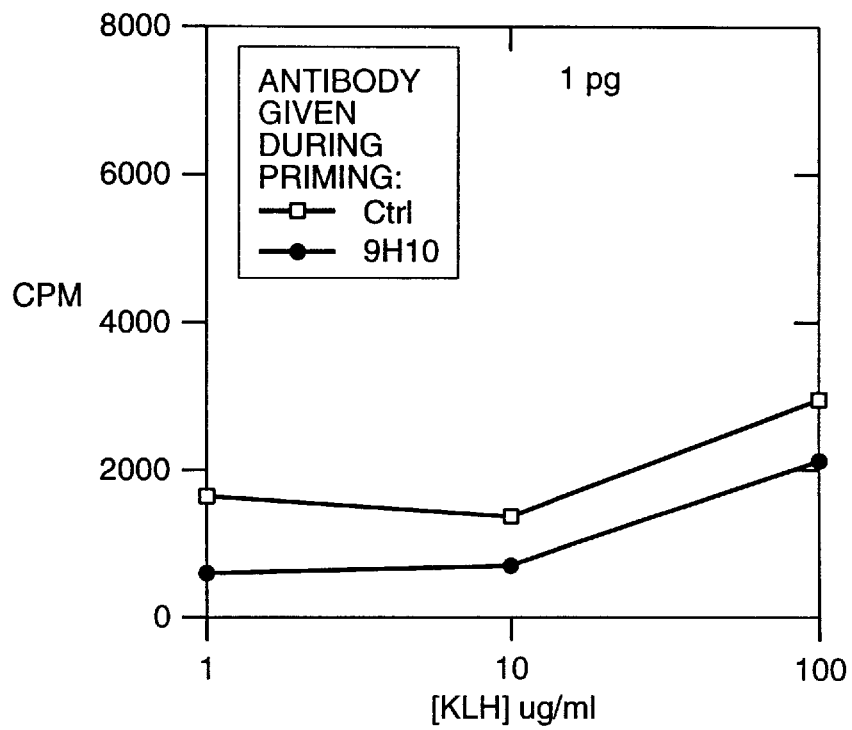
FIG._7E
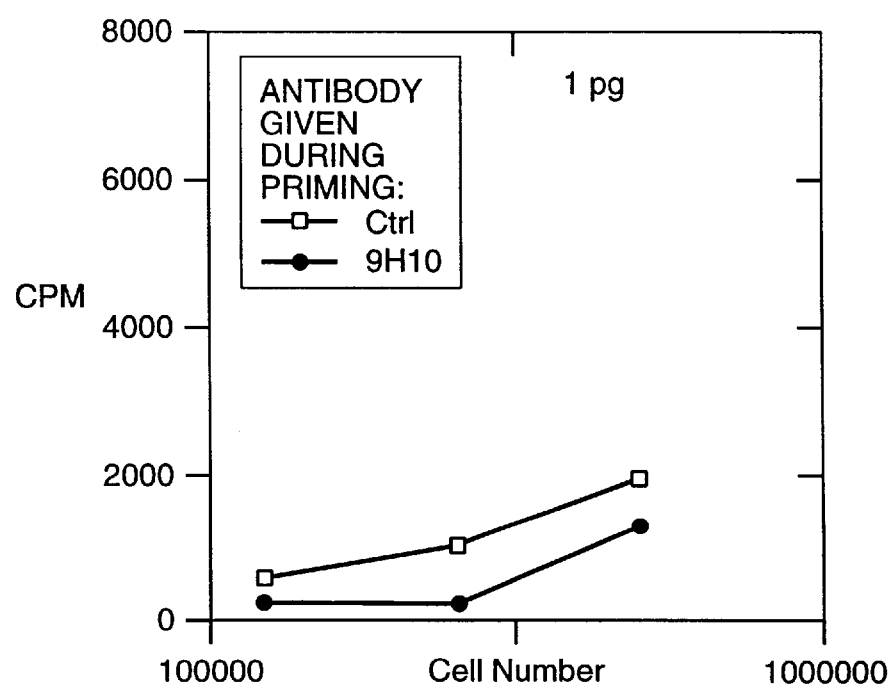
FIG._7F

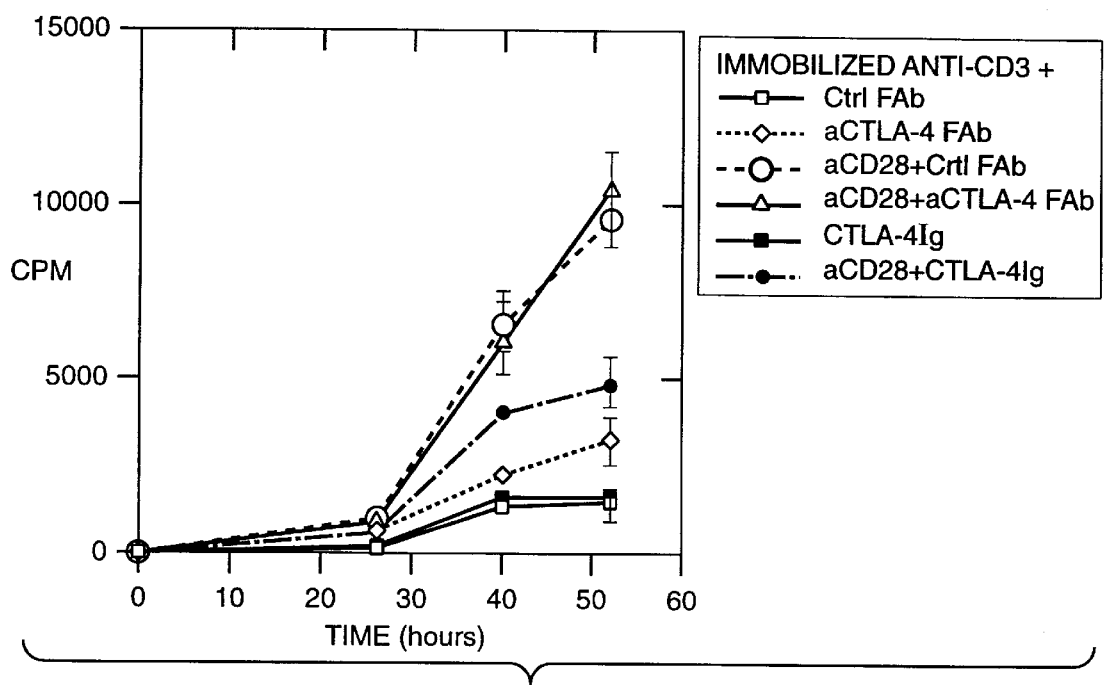
FIG._8A
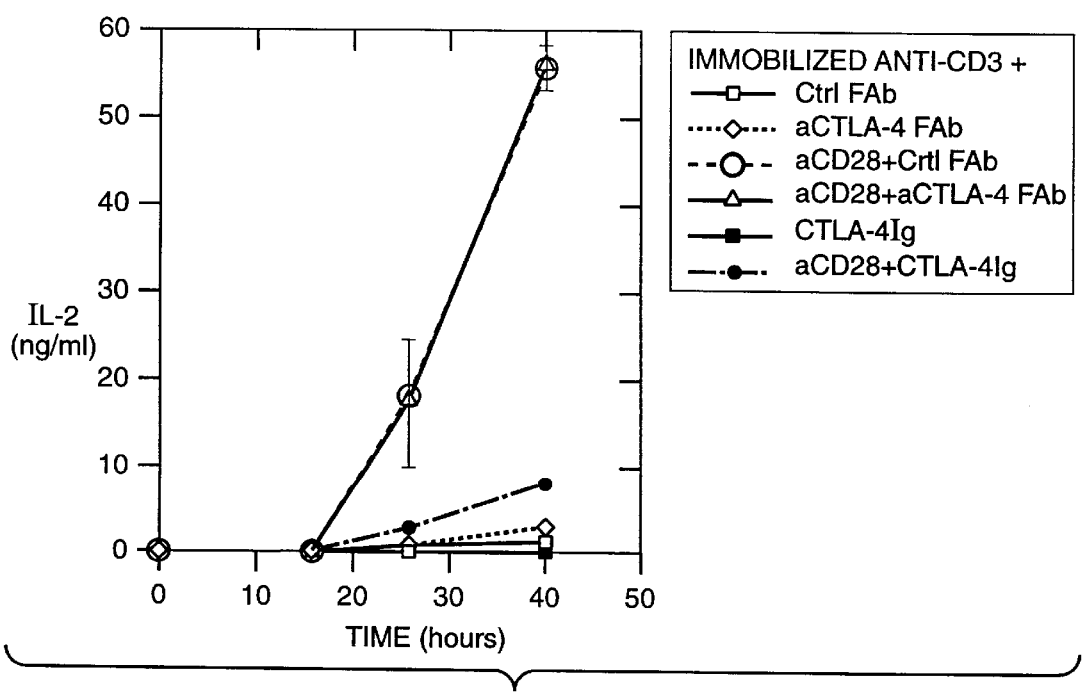
FIG._8B

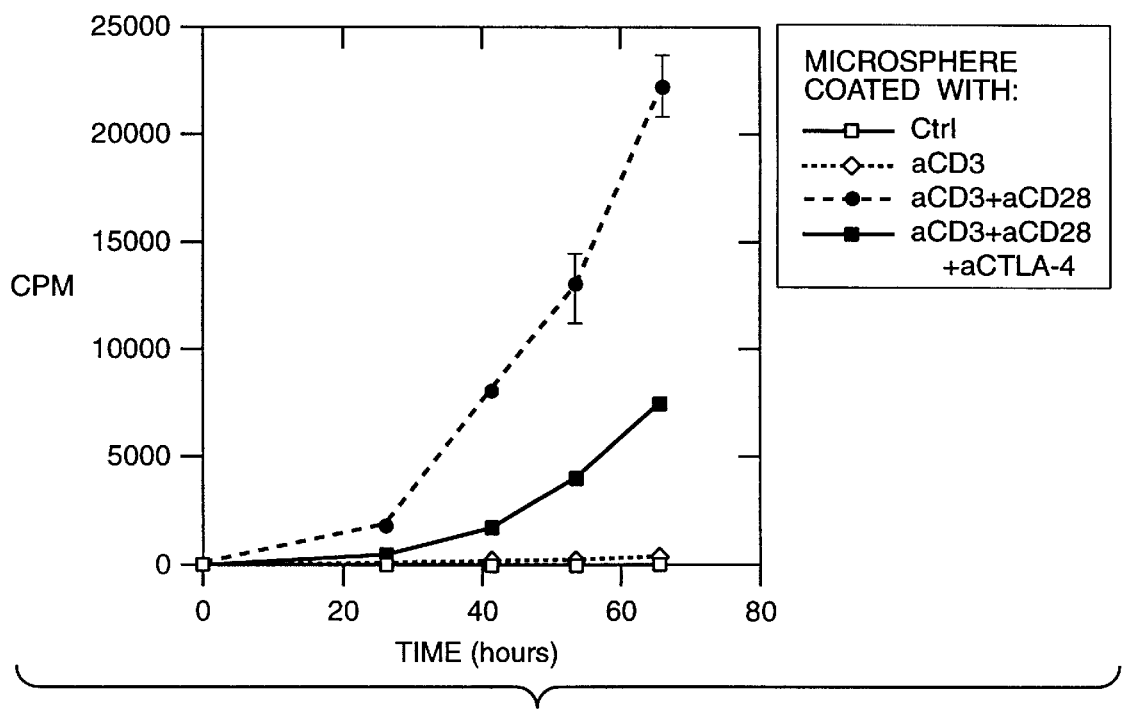
FIG._8C
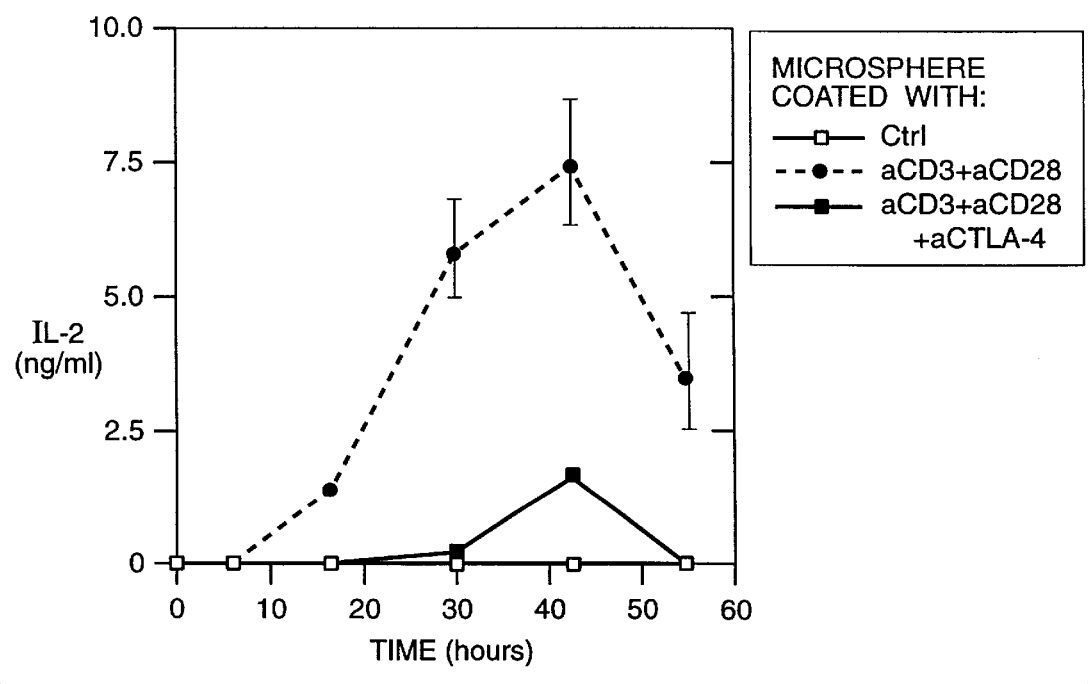
FIG._8D

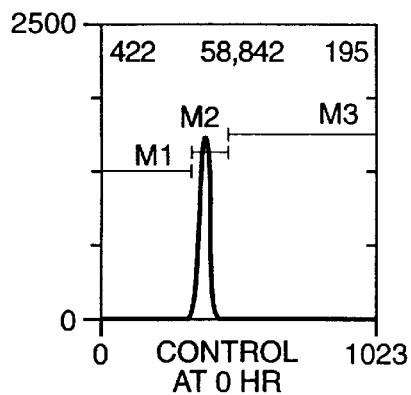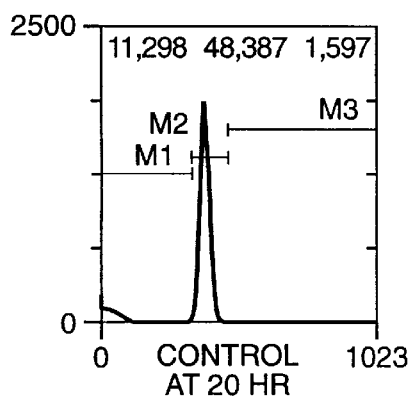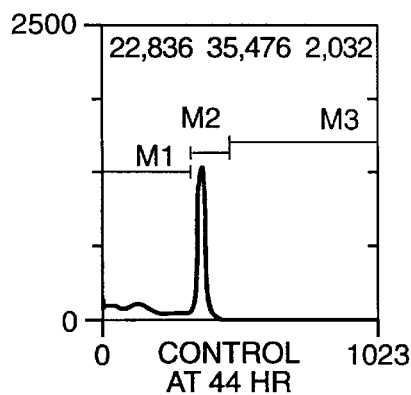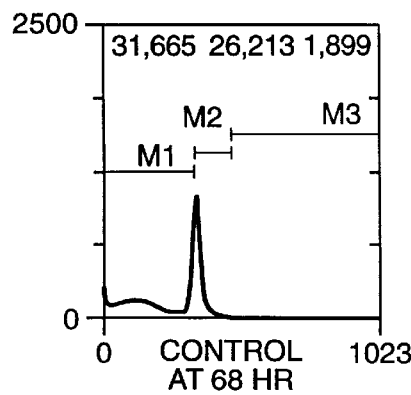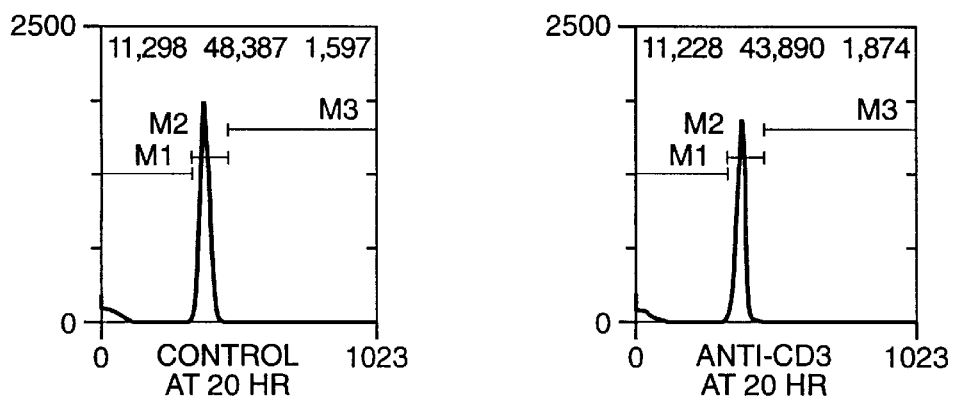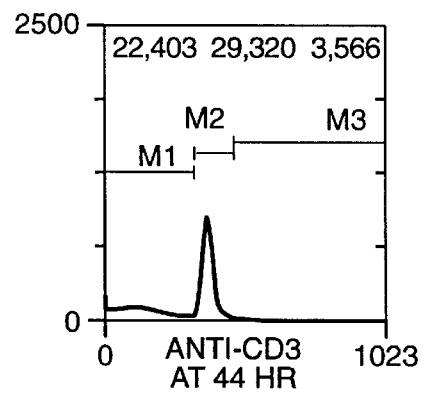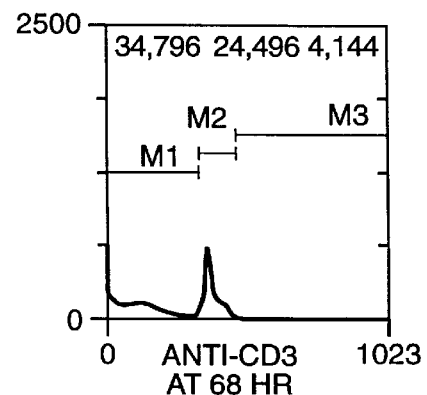
FIG._9A   FIG._9B

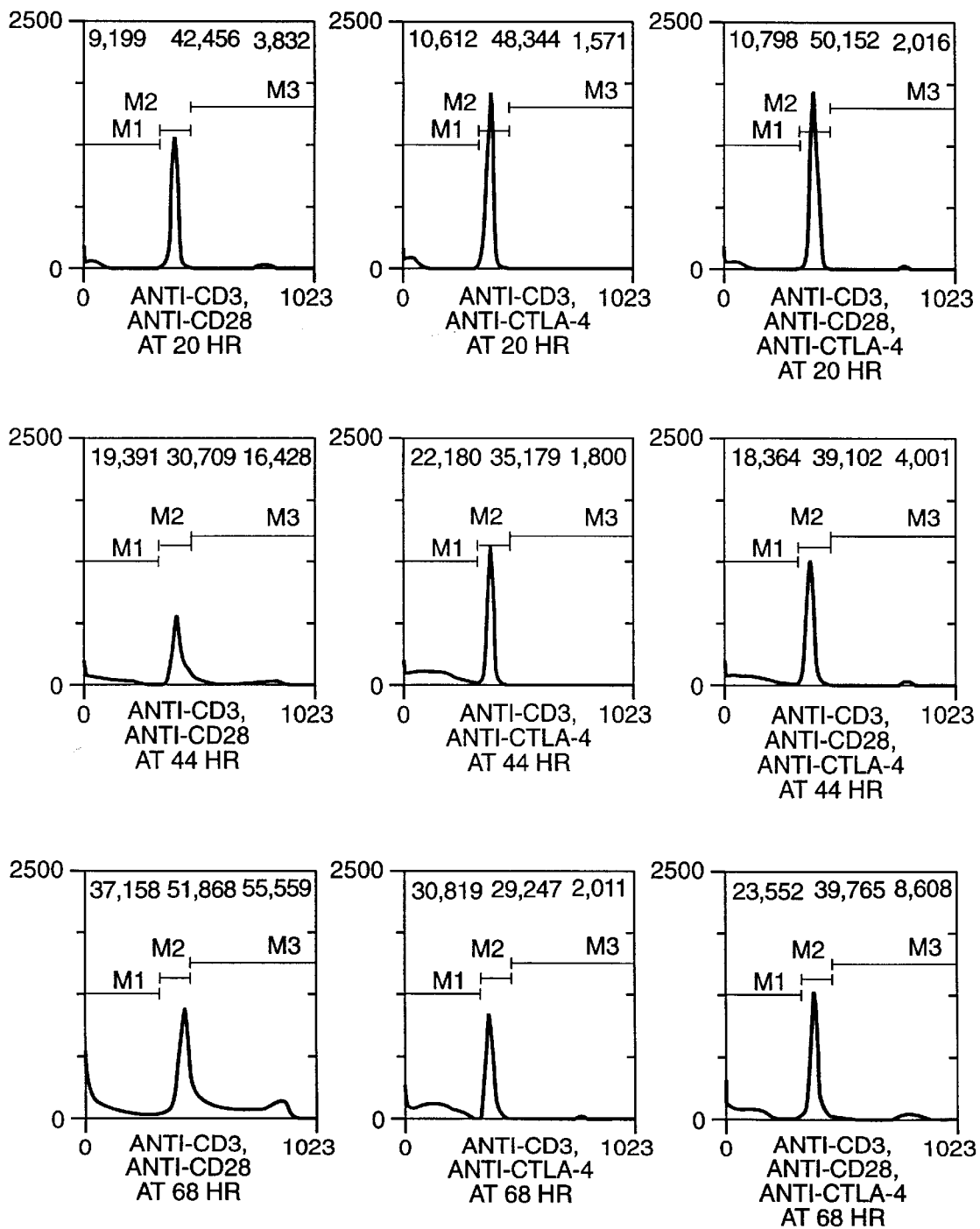
FIG._9C  FIG._9D  FIG._9E

BLOCKADE OF T LYMPHOCYTE DOWN-REGULATION ASSOCIATED WITH CTLA-4 SIGNALING

CROSS-REFERENCE TO RELATED APPLICATIONS

This application is a continuation-in-part of U.S. patent application Ser. No. 08/566,853, filed Dec. 4, 1995, which is a continuation-in-part of U.S. patent application Ser. No. 08/506,666, filed Jul. 25, 1995 now abandoned.

This invention was made with government support under Contract Nos. CA 40041 and CA 09179 awarded by the National Institutes of Health. The Government has certain rights in this invention.

INTRODUCTION

Putting immunotherapy into practice is a highly desired goal in the treatment of human disease. It promises a specificity of action that is rarely found with the use of conventional drugs. The basis for immunotherapy is the manipulation of the immune response, particularly the responses of T cells. T cells possess complex and subtle systems for controlling their interactions, utilizing numerous receptors and soluble factors for the process. The effect that any particular signal will have on the immune response may vary, depending on the factors, receptors and counter-receptors that are involved.

The pathways for down-regulating responses are as important as those required for activation. Thymic education leading to T-cell tolerance is one mechanism for preventing an immune response to a particular antigen. Other mechanisms, such as secretion of suppressive cytokines, are also known.

Activation of T cells requires not only stimulation through the antigen receptor (TCR) but additional signaling through co-stimulatory surface molecules such as CD28. The ligands for CD28 are the B7-1 (CD80) and B72 (CD86) proteins, which are expressed on antigen-presenting cells such as dendritic cells, activated B-cells or monocytes. The interaction between B7 and CD28 is one of several co-stimulatory signaling pathways that appear to be sufficient to trigger the maturation and proliferation of antigen specific T-cells.

Lack of co-stimulation, and the concomitant inadequacy of IL-2 production, prevent subsequent proliferation of the T cell and induce a state of non-reactivity termed "anergy". This is associated with a block in IL-2 gene transcription and a lack of responsiveness of the affected T cells to IL-4. Anergy may be overcome with prolonged IL-2 stimulation. A variety of viruses and tumors may block T cell activation and proliferation through direct or indirect means, thereby inducing a state of insufficient or non-reactivity of the host's immune system to infected or transformed cells. Among a number of functional T-cell disturbances, anergy may be at least partially responsible for the failure of the host to clear the pathogenic cells.

It would be advantageous if, in the treatment of infections and tumors, one could activate a strong cellular immune response through the manipulation of receptors involved in co-stimulation.

The use of B7 protein in mediating anti-tumor immunity is described in Chen et al. (1992) Cell 71:1093–1102 and Townsend and Allison (1993) Science 259:368. Schwartz (1992) Cell 71:1065 reviews the role of CD28, CTLA-4 and B7 in IL-2 production and immunotherapy. Harding et al. (1994) Nature 356:607–609 demonstrates that CD28 mediated signaling co-stimulates murine T cells and prevents the induction of anergy in T cell clones.

CTLA-4 is a T cell surface molecule that was originally identified by differential screening of a murine cytolytic T cell cDNA library, Brunet et al. (1987) Nature 328:267–270. The role of CTLA-4 as a second receptor for B7 is discussed in Linsley et al. (1991) J. Exp. Med. 174:561–569. Freeman et al. (1993) Science 262:907–909 discusses CTLA-4 in B7 deficient mice. Ligands for CTLA-4 are described in Lenschow et al. (1993) P.N.A.S. 90:11054–11058.

Linsley et al. (1992) Science 257:792–795 describes immunosuppression in vivo by a soluble form of CTLA-4. Lenschow et al. (1992) Science 257:789–792 discusses long term survival of pancreatic islet grafts induced by CTLA-4Ig. It is suggested in Walunas et al. (1994) Immunity 1:405–413, that CTLA-4 can function as a negative regulator of T cell activation.

SUMMARY OF THE INVENTION

Methods and compositions are provided for increasing the activation of T cells through a blockade of CTLA-4 signaling. Binding molecules that specifically interact with the CTLA-4 antigen, but do not activate signaling (blocking agents), are combined with T cells, in vitro or in vivo. When CTLA-4 signaling is thus blocked, the T cell response to antigen is released from inhibition. Such an enhanced response is useful for the treatment of tumors, chronic viral infections, and as an adjuvant during immunization.

BRIEF DESCRIPTION OF THE DRAWINGS

FIG. 1A is a graph illustrating the in vivo growth of the tumor cell line V51Blim10 in the presence or absence of antibodies directed against CTLA-4 or CD28. FIG. 1B is a graph illustrating the average tumor size in mice injected with $2 \times 10^6$ V51Blim10 cells and antibodies. FIG. 1C is a graph illustrating individual tumor growth size in mice injected with V51Blim10 cells.

FIG. 2 is a graph showing the in vivo growth of B7-51BLim10 tumors in the presence or absence of antibodies directed against CTLA-4 or CD28.

FIG. 3 shows the rejection of wild-type colon carcinoma cells by mice previously treated with V51BLim10 cells and anti-CTLA-4 antibody.

FIG. 4 shows the growth of established tumors after treatment with anti-CTLA-4 antibody.

FIG. 5 shows the growth of the murine fibrosarcoma SA1N in the absence or presence of anti-CTLA-4 antibodies.

FIGS. 6A to 6F illustrate the adjuvant effect of anti-CTLA-4 antibodies in the response of T cells to peptide antigens.

FIGS. 7A to 7F illustrate the effect of CTLA-4 blockade on class switching.

FIGS. 8A to 8D present a kinetic analysis of CTLA-4/B7 blockade on the proliferation of purified CD4+ T cells. In FIG. 8B, detection of IL-2 is shown. The kinetics of thymidine incorporation are shown in FIG. 8C. Shown in FIG. 8D, a pronounced inhibition of IL-2 production was observed when CTLA-4 was also engaged.

FIGS. 9A to 9E shows propidium iodide staining of permeabilized cells to measure DNA content at various stages of CTLA-4/B7 blockade in culture.

DATABASE REFERENCES FOR NUCLEOTIDE AND AMINO ACID SEQUENCES

The complete cDNA sequence of human CTLA-4 has the Genbank accession number L15006. The region of amino acids 1-37 is the leader peptide; 38-161 is the extracellular V-like domain; 162-187 is the transmembrane domain; and 188-223 is the cytoplasmic domain. Variants of the nucleotide sequence have been reported, including a G to A transition at position 49, a C to T transition at position 272, and an A to G transition at position 439. The complete DNA sequence of mouse CTLA-4 has the EMBL accession number X05719 (Brunet et al. (1987) *Nature* 328:267–270). The region of amino acids 1-35 is the leader peptide.

The complete DNA sequence of human B7-1 (CD80) has the Genbank accession number X60958; the accession number for the mouse sequence is X60958; the accession number for the rat sequence is U05593. The complete cDNA sequence of human B7-2 (CD86) has the Genbank accession number L25259; the accession number for the mouse sequence is L25606.

The genes encoding CD28 have been extensively characterized. The chicken mRNA sequence has the Genbank accession number X67915. The rat mRNA sequence has the Genbank accession number X55288. The human mRNA sequence has the Genbank accession number J02988. The mouse mRNA sequence has the Genbank accession number M34536.

DETAILED DESCRIPTION OF THE INVENTION

Methods and compositions are provided for up-regulating the response of T cells to antigenic stimulation. Binding molecules that specifically interact with cell surface CTLA-4, but do not activate CTLA-4 signaling (blocking agents), are combined with T cells. The T cell response to antigen is increased in the presence of the blocking agents. Such treatment is useful for increasing the specific immune response against tumors, chronic pathogenic infections, and as an adjuvant during immunization.

It is not necessary for the practice of the invention that the mechanism of action be understood. The data indicate that the subject therapy releases T cells from inhibitory signals mediated through CTLA-4. CTLA-4 mediated signals apparently inhibit cell cycle progression and IL-2 expression. The T cell response to antigen and co-stimulatory CD28 signaling is thereby upregulated in the presence of CTLA-4 blocking agents. The subject methods do not promote a generalized proliferation of unstimulated T cells.

The subject methods are useful where there is an inadequate T cell mediated response to an antigenic stimulus for an intended purpose. In vivo T cell mediated responses include the generation of cytolytic T cells, and the majority of antibody responses, particularly those involving class switching of immunoglobulin isotypes. The antigenic stimulus may be the presence of viral antigens on infected cells; tumor cells that express proteins or combinations of proteins in an unnatural context; parasitic or bacterial infection; or an immunization, e.g. vaccination, preparing monoclonal antibodies, etc. In vitro, the subject methods are used to increase the response of cultured T cells to antigen. Such activated T cells find use in adoptive immunotherapy, to study the mechanisms of activation, in drug screening, etc.

CTLA-4 blocking agents are molecules that specifically bind to the extracellular domain of CTLA-4 protein, and block the binding of CTLA-4 to its counter-receptors, e.g. CD80, CD86, etc. Usually the binding affinity of the blocking agent will be at least about 100 $\mu$M. The blocking agent will be substantially unreactive with related molecules to CTLA-4, such as CD28 and other members of the immunoglobulin superfamily. Molecules such as CD80 and CD86 are therefore excluded as blocking agents. Further, blocking agents do not activate CTLA-4 signaling. Conveniently, this is achieved by the use of monovalent or bivalent binding molecules. It will be understood by one of skill in the art that the following discussions of cross-reactivity and competition between different molecules is intended to refer to molecules having the same species of origin, e.g. human CTLA-4 binds human CD80 and 86, etc.

Candidate blocking agents are screened for their ability to meet this criteria. Assays to determine affinity and specificity of binding are known in the art, including competitive and non-competitive assays. Assays of interest include ELISA, RIA, flow cytometry, etc. Binding assays may use purified or semi-purified CTLA-4 protein, or alternatively may use T cells that express CTLA-4, e.g. cells transfected with an expression construct for CTLA-4; T cells that have been stimulated through cross-linking of CD3 and CD28; the addition of irradiated allogeneic cells, etc. As an example of a binding assay, purified CTLA-4 protein is bound to an insoluble support, e.g. microtiter plate, magnetic beads, etc. The candidate blocking agent and soluble, labeled CD80 or CD86 are added to the cells, and the unbound components are then washed off. The ability of the blocking agent to compete with CD80 and CD86 for CTLA-4 binding is determined by quantitation of bound, labeled CD80 or CD86. Confirmation that the blocking agent does not cross-react with CD28 may be performed with a similar assay, substituting CD28 for CTLA-4. Suitable molecules will have at least about $10^3$ less binding to CD28 than to CTLA-4, more usually at least about $10^4$ less binding.

Generally, a soluble monovalent or bivalent binding molecule will not activate CTLA-4 signaling. A functional assay that detects T cell activation may be used for confirmation. For example, a population of T cells may be stimulated with irradiated allogeneic cells expressing CD80 or CD86, in the presence or absence of the candidate blocking agent. An agent that blocks CTLA-4 signaling will cause an increase in the T cell activation, as measured by proliferation and cell cycle progression, release of IL-2, upregulation of CD25 and CD69, etc. It will be understood by one of skill in the art that expression on the surface of a cell, packaging in a liposome, adherence to a particle or well, etc. will increase the effective valency of a molecule.

Blocking agents are peptides, small organic molecules, peptidomimetics, soluble T cell receptors, antibodies, or the like. Antibodies are a preferred blocking agent. Antibodies may be polyclonal or monoclonal; intact or truncated, e.g. F(ab')$_2$, Fab, Fv; xenogeneic, allogeneic, syngeneic, or modified forms thereof, e.g. humanized, chimeric, etc.

In many cases, the blocking agent will be an oligopeptide, e.g. antibody or fragment thereof, etc., but other molecules that provide relatively high specificity and affinity may also be employed. Combinatorial libraries provide compounds other than oligopeptides that have the necessary binding characteristics. Generally, the affinity will be at least about $10^{-6}$, more usually about $10^{-8}$M, i.e. binding affinities normally observed with specific monoclonal antibodies.

A number of screening assays are available for blocking agents. The components of such assays will typically include CTLA-4 protein; and optionally a CTLA-4 activating agent, e.g. CD80, CD86, etc. The assay mixture will also comprise a candidate pharmacological agent. Generally a plurality of assay mixtures are run in parallel with different agent concentrations to obtain a differential response to the various concentrations. Typically, one of these concentrations serves as a negative control, i.e. at zero concentration or below the level of detection.

Conveniently, in these assays one or more of the molecules will be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule which provides for detection, in accordance with known procedures.

One screening assay of interest is directed to agents that interfere with the activation of CTLA-4 by its counter-receptors. Quantitation of activation may be achieved by a number of methods known in the art. For example, the inhibition of T cell activation may be determined by quantitating cell proliferation, release of cytokines, etc.

Other assays of interest are directed to agents that block the binding of CTLA-4 to its counter-receptors. The assay mixture will comprise at least a portion of the natural counter-receptor, or an oligopeptide that shares sufficient sequence similarity to provide specific binding, and the candidate pharmacological agent. The oligopeptide may be of any length amenable to the assay conditions and requirements, usually at least about 8 aa in length, and up to the full-length protein or fusion thereof. The CTLA-4 may be bound to an insoluble substrate. The substrate may be made in a wide variety of materials and shapes e.g. microtiter plate, microbead, dipstick, resin particle, etc. The substrate is chosen to minimize background and maximize signal to noise ratio. Binding may be quantitated by a variety of methods known in the art. After an incubation period sufficient to allow the binding to reach equilibrium, the insoluble support is washed, and the remaining label quantitated. Agents that interfere with binding will decrease the detected label.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl, sulfhydryl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

A variety of other reagents may be included in the screening assay. These include reagents like salts, neutral proteins, e.g. albumin, detergents, etc which may be used to facilitate optimal protein-DNA binding and/or reduce non-specific or background interactions. Also reagents that otherwise improve the efficiency of the assay, such as protease inhibitors, nuclease inhibitors, anti-microbial agents, etc. may be used.

Suitable antibodies for use as blocking agents are obtained by immunizing a host animal with peptides comprising all or a portion of CTLA-4 protein. Suitable host animals include mouse, rat, sheep, goat, hamster, rabbit, etc. The origin of the protein immunogen may be mouse, human, rat, monkey etc. The host animal will generally be a different species than the immunogen, e.g. mouse CTLA-4 used to immunize hamsters, human CTLA-4 to immunize mice, etc. The human and mouse CTLA-4 contain highly conserved stretches in the extracellular domain (Harper et al. (1991) *J. Immunol.* 147:1037–1044). Peptides derived from such highly conserved regions may be used as immunogens to generate cross-specific antibodies.

The immunogen may comprise the complete protein, or fragments and derivatives thereof. Preferred immunogens comprise all or a part of the extracellular domain of human CTLA-4 (amino acid residues 38-161), where these residues contain the post-translation modifications, such as glycosylation, found on the native CTLA-4. Immunogens comprising the extracellular domain are produced in a variety of ways known in the art, e.g. expression of cloned genes using conventional recombinant methods, isolation from T cells, sorted cell populations expressing high levels of CTLA-4, etc.

Where expression of a recombinant or modified protein is desired, a vector encoding the desired portion of CTLA-4 will be used. Generally, an expression vector will be designed so that the extracellular domain of the CTLA-4 molecule is on the surface of a transfected cell, or alternatively, the extracellular domain is secreted from the cell. When the extracellular domain is to be secreted, the coding sequence for the extracellular domain will be fused, in frame, with sequences that permit secretion, including a signal peptide. Signal peptides may be exogenous or native. A fusion protein of interest for immunization joins the CTLA-4 extracellular domain to the constant region of an immunoglobulin. For example, a fusion protein comprising the extracellular domain of mouse CTLA-4 joined to the hinge region of human Cγ1 (hinge-CH2-CH3) domain may be used to immunize hamsters.

When the CTLA-4 is to be expressed on the surface of the cell, the coding sequence for the extracellular domain will be fused, in frame, with sequences encoding a peptide that anchors the extracellular domain into the membrane and a signal sequence. Such anchor sequences include the native CTLA-4 transmembrane domain, or transmembrane domains from other cell surface proteins, e.g. CD4, CD8, slg, etc. Mouse cells transfected with the human CTLA-4 gene may be used to immunize mice and generate antibodies specific for the human CTLA-4 protein.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using CTLA-4 bound to an insoluble support, protein A sepharose, etc.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the blocking agent. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segements to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

Situations characterized by deficient host T cell response to antigen include chronic infections, tumors, immunization with peptide vaccines, and the like. Administration of the subject CTLA-4 blockers to such hosts specifically changes the phenotype of activated T cells, resulting in increased response to antigen mediated activation. Treatment of primates, more particularly humans is of interest, but other mammals may also benefit from treatment, particularly domestic animals such as equine, bovine, ovine, feline, canine, murine, lagomorpha, and the like.

The formulation is administered at a dose effective to increase the response of T cells to antigenic stimulation. The response of activated T cells will be affected by the subject treatment to a greater extent than resting T cells. The determination of the T cell response will vary with the condition that is being treated. Useful measures of T cell activity are proliferation, the release of cytokines, e.g. IL-2, IFNγ, TNFα; T cell expression of markers such as CD25 and CD69; and other measures of T cell activity as known in the art.

The subject treatment may be performed in combination with administration of cytokines that stimulate antigen presenting cells, e.g. granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), etc. Additional proteins and/or cytokines known to enhance T cell proliferation and secretion, such as IL-1, IL-2, B7, anti-CD3 and anti-CD28 can be employed simultaneously or sequentially with the blocking agents to augment the immune response. The subject therapy may be combined with the transfection of tumor cells or tumor-infiltrating lymphocytes with genes encoding for various cytokines or cell surface receptors (see Ogasawara et al. (1993) *Cancer Res.* 53:3561–8; and Townsend et al. (1993) *Science* 259:368–370). For example, it has been shown that transfection of tumor cells with cDNA encoding CD80 leads to rejection of transfected tumor cells, and can induce immunity to a subsequent challenge by the non-transfected parent tumor cells (Townsend et al. (1994) *Cancer Res.* 54:6477–6483). The subject therapy enhances this effect.

Tumor-specific host T cells may be combined ex vivo with the subject blocking agents, and tumor antigens or cells and reinfused into the patient. When administered to a host, the stimulated cells induce a tumoricidal reaction resulting in tumor regression. The host cells may be isolated from a variety of sources, such as lymph nodes, e.g. inguinal, mesenteric, superficial distal auxiliary, etc.; bone marrow; spleen; or peripheral blood, as well as from the tumor, e.g. tumor infiltrating lymphocytes. The cells may be allogeneic or, preferably, autologous. For ex vivo stimulation, the host cells are aseptically removed, and are suspended in any suitable media, as known in the art. The cells are stimulated by any of a variety of protocols, particularly combinations of B7, anti-CD28, etc., in combination with the blocking agents. The stimulated cells are reintroduced to the host by injection, e.g. intravenous, intraperitoneal, etc. in a variety of pharmaceutical formulations, including such additives as binder, fillers, carriers, preservatives, stabilizing agents, emulsifiers and buffers. Suitable diluents and excipients are water, saline, glucose and the like.

Tumor cells whose growth may be decreased by administration of the subject blocking agents include carcinomas e.g. adenocarcinomas, which may have a primary tumor site in the breast, ovary, endometrium, cervix, colon, lung, pancreas, eosophagus, prostate, small bowel, rectum, uterus or stomach; and squamous cell carcinomas, which may have a primary site in the lungs, oral cavity, tongue, larynx, cavity, tongue, larynx, eosophagus, skin, bladder, cervix, eyelid, conjunctiva, vagina, etc. Other classes of tumors that may be treated include sarcomas, e.g. myogenic sarcomas; neuromas; melanomas; leukemias, certain lymphomas, trophoblastic and germ cell tumors; neuroendocrine and neuroectodermal tumors.

Tumors of particular interest are those that present tumor-specific antigens. Such antigens may be present in an abnormal context, at unusually high levels, or may be mutated forms. The tumor antigen may be administered with the subject blocking agents to increase the host T cell response against the tumor cells. Such antigen preparations may comprise purified protein, or lysates from tumor cells.

Examples of tumors antigens are cytokeratins, particularly cytokeratin 8, 18 and 19, as an antigen for carcinomas. Epithelial membrane antigen (EMA), human embryonic antigen (HEA-125); human milk fat globules, MBr1, MBr8, Ber-EP4, 17-1A, C26 and T16 are also known carcinoma antigens. Desmin and muscle-specific actin are antigens of myogenic sarcomas. Placental alkaline phosphatase, beta-human chorionic gonadotropin, and alpha-fetoprotein are antigens of trophoblastic and germ cell tumors. Prostate specific antigen is an antigen of prostatic carcinomas, carcinoembryonic antigen of colon adenocarcinomas. HMB45 is an antigen of melanomas. Chromagranin-A and synaptophysin are antigens of neuroendocrine and neuroectodermal tumors. Of particular interest are aggressive tumors that form solid tumor masses having necrotic areas. The lysis of such necrotic cells is a rich source of antigens for antigen-presenting cells.

Administration of the subject blocking agents may be contra-indicated for certain lymphomas. In particular, T cell lymphomas may not benefit from increased activation. CD80 antigen is strongly expressed by the Reed-Sternberg cells in Hodgkin's disease, which are frequently surrounded by CD28-expressing T cells (Delabie et al. (1993) *Blood* 82:2845–52). It has been suggested that the accessory cell function of Reed-Sternberg cells leads to T cell activation, and contributes to the Hodgkin's syndrome.

Many conventional cancer therapies, such as chemotherapy and radiation therapy, severely reduce lymphocyte populations. While the subject therapy may alleviate this immunosuppression to some extent, a preferred course of combined treatment will use such lymphotoxic therapies before or after the subject therapy.

The subject blocking agents may be administered to increase the response of T cells to pathogens. Infections with certain viruses become chronic when the host anti-viral mechanisms fail. Such infections can persist for many years or even the life-time of the infected host, and often cause serious disease. Chronic infections associated with significant morbidity and early death include those with two human hepatitis viruses, hepatitis B virus (HBV) and hepatitis C virus (HCC), which cause chronic hepatitis, cirrhosis and liver cancer. Other chronic viral infections in man include those with human retroviruses: human immunodeficiency viruses (HIV-1 and HIV-2) which cause AIDS and human T lymphotropic viruses (HTLV-1 and HTLV-2) which cause T cell leukemia and myelopathies. Infections with human herpes viruses including herpes simplex virus (HSV) types 1 and 2, Epstein Barr virus (EBV), cytomegalovirus (CMV) varicella-zoster virus (VZV) and human herpes virus 6 (HHV-6) are usually not eradicated by host mechanisms. Infection with other agents that replicate intracellularly, such as pathogenic protozoa, e.g. trypanosomes, malaria and toxoplasma gondii; bacteria, e.g. mycobacteria, salmonella and listeria; and fungi, e.g. candida; may also become chronic when host defense mechanisms fail to eliminate them.

The subject blocking agents are administered to a patient suffering from such a chronic pathogen infection. To increase the immune response, it may be desirable to formulate the blocking agent with antigens derived from the pathogen. A variety of such antigens are known in the art, and available by isolation of the pathogen or expression by recombinant methods. Examples include HIV gp 120, HBV surface antigen, envelope and coat proteins of viruses, etc.

Adjuvants potentiate the immune response to an antigen. The CTLA-4 blocking agents are used as an adjuvant to increase the activation of T cells, and to increase the class switching of antibody producing cells, thereby increasing the concentration of IgG class antibodies produced in response to the immunogen. The blocking agents are combined with an immunogen in a physiologically acceptable medium, in accordance with conventional techniques for employing adjuvants. The immunogen may be combined in a single formulation with the blocking agent, or may be administered separately. Immunogens include polysaccharides, proteins, protein fragments, haptens, etc. Of particular interest is the use with peptide immunogens. Peptide immunogens may include tumor antigens and viral antigens or fragments thereof, as described above.

The use of the subject blocking agents in conjunction with genetic immunization is also of interest. A DNA expression vector encoding a peptide or protein antigen of interest is injected into the host animal, generally in the muscle or skin. The gene products are correctly glycosylated, folded and expressed by the host cell. The method is advantageous where the antigens are difficult to obtain in the desired purity, amount or correctly glycosylated form or when only the genetic sequences are known e.g. HCV. Typically, DNA is injected into muscles or delivered coated onto gold microparticles into the skin by a particle bombardment device, a "gene gun". Genetic immunization has demonstrated induction of both a specific humoral but also a more broadly reacting cellular immune response in animal models of cancer, mycoplasma, TB, malaria, and many virus infections including influenza and HIV. See, for example, Mor et al. (1995) *J Immunol* 155:2039–46; Xu and Liew (1995) Immunology 84:173–6; and Davis et al. (1994) Vaccine 12:1503–9.

The subject blocking agents are used during the immunization of laboratory animals, e.g. mice, rats, hamsters, rabbits, etc. for monoclonal antibody production. The administration increases the level of response to the antigen, and increases the proportion of plasma cells that undergo class switching.

CTLA-4 blockers are administered in vitro to increase the activation of T cells in culture, including any in vitro cell culture system, e.g. immortalized cell lines, primary cultures of mixed or purified cell populations, nontransformed cells, etc. Of particular interest are primary T cell cultures, where the cells may be removed from a patient or allogeneic donor, stimulated ex vivo, and reinfused into the patient.

Various methods for administration may be employed. The CTLA-4 blocking agent formulation may be injected intravascularly, subcutaneously, peritoneally, etc. The dosage of the therapeutic formulation will vary widely, depending upon the nature of the disease, the frequency of administration, the manner of administration, the purpose of the administration, the clearance of the agent from the host, and the like. The dosage administered will vary depending on known factors, such as the pharmacodynamic characteristics of the particular agent, mode and route of administration, age, health and weight of the recipient, nature and extent of symptoms, concurrent treatments, frequency of treatment and effect desired. The dose may be administered as infrequently as weekly or biweekly, or fractionated into smaller doses and administered daily, semi-weekly, etc. to maintain an effective dosage level. Generally, a daily dosage of active ingredient can be about 0.1 to 100 mg/kg of body weight. Dosage forms suitable for internal administration generally contain from about 0.1 mg to 500 mgs of active ingredient per unit. The active ingredient may vary from 0.5 to 95% by weight based on the total weight of the composition.

In some cases it may be desirable to limit the period of treatment due to excessive T cell proliferation. The limitations will be empirically determined, depending on the response of the patient to therapy, the number of T cells in the patient, etc. The number of T cells may be monitored in a patient by methods known in the art, including staining with T cell specific antibodies and flow cytometry.

The subject CTLA-4 blockers are prepared as formulations at an effective dose in pharmaceutically acceptable media, for example normal saline, vegetable oils, mineral oil, PBS, etc. Therapeutic preparations may include physiologically tolerable liquids, gel or solid carriers, diluents, adjuvants and excipients. Additives may include bactericidal agents, additives that maintain isotonicity, e.g. NaCl, mannitol; and chemical stability, e.g. buffers and preservatives. or the like. The CTLA-4 blockers may be administered as a cocktail, or as a single agent. For parenteral administration, the blocking agent may be formulated as a solution, suspension, emulsion or lyophilized powder in association with a pharmaceutically acceptable parenteral vehicle. Liposomes or non-aqueous vehicles, such as fixed oils, may also be used. The formulation is sterilized by techniques as known in the art.

The functional effect of CTLA-4 blockade may also be induced by the administration of other agents that mimic the change in intra-cellular signaling observed with the subject invention. For example, it is known that specific cytoplasmic kinases may be activated in response to binding of extracellular receptors. Agents that block the kinase activity would have a similar physiological effect as blocking receptor binding. Similarly, agents that increase cyclic AMP, GTP concentrations and intracellular calcium levels can produce physiological effects that are analagous to those observed with extracellular receptor binding.

The following examples are offered by way of illustration and not by way of limitation.

EXPERIMENTAL

EXAMPLE 1

Generation of Monoclonal Antibodies Reactive
With Mouse CTLA-4 a) Preparation of a Mouse CTLA-4 Immunogen

A fusion protein comprising the extracellular portions of the mouse CTLA-4 gene and the constant region of human IgGI, termed mCTLA4-Hγl, was obtained from Drs. P. Lane and K. Karjalainen (Basel Institute for Immunology, Basel, Switzerland). An expression vector capable of expressing the mCTLA4-Hγl protein was constructed as described [Lane, et al. *Immunol.* 80:56 (1993)]. Briefly, sequences encoding the extracellular portions of the mouse CTLA-4 molecule were generated using PCR. The following primer pair was used to amplify these CTLA-4 sequences from a plasmid containing mouse CTLA-4 sequences: 5'-TTACTCTACTCCCTGAGG AGCTCAGCACATTTGCC-3' (SEQ ID NO:1) and 5'-TATACTTACCAGMTCCG GGCATGGTTCTGGATCA-3' (SEQ ID NO:2). The amplified CTLA-4 sequences were then inserted into an expression vector that permits the insertion of a gene of interest upstream of sequences encoding the hinge, CH2 and CH3 domains of the human IgG1 protein [Traunecker, et al. *Trends Biotech.* 9:109 (1991)]. Each primer contained appropriate restriction sites for subcloning into the human IgG1 expression vector, together with a 3' splice donor site within the 3' primer to splice to the human γl exons correctly. The plasmid containing sequences encoding the mCTLA-4-Hγl fusion protein was termed pH β-APr-1-neo-mCTLA4-Hγl. The amino acid sequence of the mCTLA4-Hγl protein is listed in SEQ ID NO:3.

To express the mCTLA4-Hγl protein, the pHβAPr-1-neo-mCTLA4-Hγl expression vector was transfected into the mouse plasmacytoma line, J558L (J558L is identical to the J558 cell line which is available from ATCC [ATCC TlB 6]) using the standard technique of protoplast fusion. J558L cells were cultured at $5\times10^4$ cells/ml. Transfected J558L cells were then selected in the presence of medium containing xanthine (Sigma) and mycophenolic acid (Calbiochem, LaJolla, Calif.) (selective medium). The selective medium was applied 24 hr after transfection and positive clones (ie., clones which grew in the selective medium) were screened two weeks later. Clones that secreted the fusion protein were identified using an ELISA for human IgG1. A good secreting clone was identified and designated clone no. 15. Clone no. 15 cells were metabolically labelled with [$^{35}$S]methionine and the secreted proteins were immunoprecipitated with protein A and the precipitated proteins were resolved on an SDS polyacrylamide gel. The mCTLA4-Hγl protein was found to migrate on SDS-PAGE gels as a monomer of approximately 60,000 MW under reducing conditions and as a dimer under non-reducing conditions.

Purified preparations of mCTLA4-Hγl protein were obtained by affinity chromatography of culture supernatants of clone no. 15 cells on a protein A-Sepharose (Zymed, South San Francisco, Calif.) column. Briefly, J558 cells expressing the mCTLA4-Hγl protein were grown in IMDM supplemented with 5% FCS, glutamine, 2ME and antibiotics. Culture supernatants were collected from the cells and centrifuged at 1500×g to remove any remaining cells and the clarified supernatant was filtered through a 0.4 micron pore size. The filtered supernatant was adjusted to pH 8.5 using 1N NaOH; the supernatant was then passed over a 2 ml (packed volume) protein A-Sepharose column at a flow rate of 2 ml/min. It is noted that the J558 cell line produces an additional immunoglobulin (i.e., besides the mouse CTLAlg fusion protein) that binds to protein G; therefore the use of protein G resins is not recommended for the purification of the mCTLA4-Hγl protein from transfected J558 cells.

The protein A column was washed with 20 to 30 column volumes of PBS and the fusion protein was eluted with 50 mM diethylamine (pH 11.0). Two milliliter fractions were collected into tubes containing 0.2 ml 1M Tris-HCl to neutralize the pH of the sample. The absorbance at 280 nm was determined and used to assess the protein concentration of each fraction. Fractions containing protein were combined and dialyzed overnight against 2 to 3 changes of PBS (1 liter per change). The presence of mCTLA4-Hγl protein was confirmed by SDS-PAGE, which showed a band of approximately 40 kD (the predicted molecular weight of the fusion protein). In addition, the purified mCTLA4-Hγl protein was tested in an ELISA using an antihuman IgG1 antibody (HP6058; the HP6058 hybridoma (ATCC CRL 1786) was used as the source of HP6058 antibodies).

b) Immunization of Hamsters

To immunize hamsters with the mouse CTLA-4 fusion protein, purified mCTLA4-Hγl protein (hereafter referred to as CTLA-4Ig) was used to coat heat-killed *Staphylococcus aureus* (StaphA) bacteria cells (Calbiochem, LaJolla, Calif.). Six week old Golden Syrian hamsters (Harlan Sprague Dawley, Indianapolis, Ind.) were injected in the footpad with 50 μl (packed volume) of heat-killed StaphA bacteria coated with approximately 100 μg of CTLA-4Ig suspended in 0.2 ml of PBS. The StaphA cells were coated as follows.

StaphA cells were prepared according to the manufacturer's protocol to a concentration of 10% w/v in saline (0.9% NaCl). One ml of the bacterial cell slurry was centrifuged at 1,400×g to pellet the bacteria and the supernatant was removed. A 1 ml solution containing approximately 100 μg of purified CTLA-4Ig in PBS was added to the pellet and the mixture was incubated at 37° C. for 2 hours with agitation. The bacteria were then pelleted by centrifugation as described above; the pellet was washed twice with 1 ml of PBS/wash. The CTLA-4Ig-coated bacterial cells were then resuspended in approximately 200 μl of PBS; 50 μl of this preparation was injected per footpad.

A total of five injections were given per hamster. On the day of the final boost and prior to the injection, approximately 100 μl of serum was obtained by intraocular bleeding performed by the Office of Laboratory Animal Care staff (Univ. of Calif, Berkeley). This serum was analyzed in comparison to serum obtained by the identical methodology prior to the first injection.

A CTLA-4Ig binding ELISA was utilized to demonstrate the presence of antibody that recognized the CTLA-4Ig fusion protein in the post-immunization bleed. The CTLA-4Ig binding ELISA was conducted as follows. CTLA-4Ig fusion protein or CD4Ig fusion protein was used to coat the wells of 96 well modified flatbottom ELISA plates (Corning, Corning, N.Y.).

CD4Ig is a fusion protein that consists of the extracellular domain of mouse CD4 and the hinge, CH2 and CH3 domains of human IgG1 [Traunecker et al., supra.]; the CD4Ig protein was used as a negative control in the ELISA assays. The CD4Ig fusion protein was prepared from transfected J558 cells and purified by affinity chromatography on protein A Sepharose as described for the mCTLA4-Hμl (i.e., the CTLA-4Ig) fusion protein in section (a) above.

Fifty microliters of the fusion proteins, at a concentration of 1 μg/ml in 0.4% gelatin in PBS were placed in the wells. The plates were incubated at 37° C. for 2–3 hours to allow the proteins to absorb; the plates were then washed three times using 150 μl of 0.9% NaCl containing 0.05% Tween-20. The remaining protein binding sites in the wells were then blocked using 0.4% gelatin in PBS (blocking buffer) for 30 min at 37° C.; following the blocking step, the plates were washed twice with 0.9% NaCl containing 0.05% Tween-20. Fifty microliters of solution containing antiCTLA-4 antibodies (i.e., serum from immunized hamsters, purified antibodies or culture supernatants) were added into triplicate wells and the plates were incubated for 2–3 hours at 37° C. To assess the amount of anti-CTLA-4 antibodies present in the serum of immunized hamsters, the initial post-immunization bleeds were tested using dilutions ranging from 1:1000 to 1:100 (diluted into PBS containing 0.4% gelatin).

The wells were then washed three times using 150 μl of 0.9% NaCl containing 0.05% Tween-20. Fifty microliters of a solution containing goat anti-hamster IgG polyclonal sera conjugated to horseradish peroxidase (CalTag, South San Francisco, Calif.) at a concentration of 1 μg/ml in blocking buffer was added to the wells and the plates were incubated for 1 hour at 37° C. The plates were then washed four times with 0.9% NaCl containing 0.05% Tween-20. A solution containing 0.55 mg/ml ABTS 2,2'-Azino-bis (3-ethylbenzthiazoline-6-sulfonic acid)] in citrate buffer [0.1M citric acid (pH 4.35)] was added and the plates were incubated for approximately 20 min at 37° C. The plates were then read at 405 nm using a BioTech plate reader (Beckman Instruments, Palo Alto, Calif.) to assess the absorbance of the green reaction product.

The results of the CTLA-4Ig binding ELISA demonstrated the presence of antibody that recognized the CTLA-4Ig fusion protein in the post-immunization bleed at serum dilutions 1000-fold greater than the dilution at which background could be detected using the pre-immune bleed.

c) Isolation of Hybridoma Lines Secreting Anti-mouse CTLA-4 Antibodies

Three days following the final injection, draining lymph nodes were removed from the hamsters. Lymphocytes were isolated from the popliteal lymph nodes which drain the hind-limbs. Cell suspensions were made from the isolated lymph nodes as follows. The dissected nodes were placed in a tissue culture dish (Falcon Plastics, Mountain View, Calif.) containing RPMI medium (GibcoBRL, Gaithersburg, Md.) supplemented with 10% FCS (BioWhittaker, Walkersville, Md.). Lymphocytes were released from the nodes by gentle grinding of the nodes with frosted glass slides; the lymphocyte suspensions were counted using a hemocytometer.

The lymphocytes isolated from the immunized hamsters were fused to the fusion cell partner, P3X3.Ag8.653 (ATCC CRL 1580). P3X3.Ag8.653 cells were split 1:20 every 3 days prior to the fusion in IMDM (Univ. of Calif., San Francisco Tissue Culture Facility) containing 20% FCS (fetal calf serum) (BioWhittaker, Walkersville, Md.), 50 μM 2-ME, 50 μM gentamicin.

The fusion with the myeloma line used a standard polyethylene glycol fusion technique [McKearn et al., Immunol. Rev. 47:91 (1979)]. Briefly, sterile lymphocyte cell suspensions were prepared in serum free Iscove's Modified Dulbecco's Media (IMDM). The lymphocytes were washed twice with IMDM and adjusted to a density of $12.5 \times 10^6$ cells/ml.

P3X3.Ag8.653 cells (grown as described above) were washed twice with serum free IMDM [these cells were centrifuged for 5 minutes at 1000 r.p.m. in a TJ-6 centrifuge (Beckman Instruments, Palo Alto, Calif.) at 25° C. to pellet the cells] and the P3X3.Ag8.653 cell density was adjusted to $5\times10^6$ cells/ml.

Four milliliters of the lymphocyte cell suspension were mixed with 1 ml of the washed P3X3.Ag8.653 cells in 60 mm tissue culture dish (Falcon). The tissue culture dishes were placed in microtiter plate carriers (Beckman Instruments, Palo Alto, Calif.) and centrifuged at 250×g (1200 r.p.m.; TJ-6 centrifuge) for 5 minutes to generate an adherent monolayer of cells on the bottom of the dish. The supernatant was aspirated from the dishes and the dishes were neatly flooded with 1 ml of 50% polyethylene glycol (PEG 1500, Boehringer Mannheim) in IMDM; the PEG solution was prepared by warming 4 ml of PEG 1500 and 4 ml of IMDM separately in 60° C. water bath and then combining by aspiration of the PEG into a pipette followed by the IMDM and mixing thoroughly. After 30 seconds at room temperature, the dishes were flooded with 5 ml of serum free IMDM.

Following the final wash on the day of the fusion, the cells were left in the 60 mm dish with 5 ml of IMDM medium containing FCS for 12 hours at 37° C. with 5% $CO_2$. On the following day, the fused cells were diluted into 100 ml of IMDM containing 20% FCS and 1×HAT media (Boehringer Mannheim, N.J.) and 100 μl was plated per well in 96 well flat bottom plates. After 5 and 9 days, an additional 50 μl of media was added to each well. Thereafter, 50 μl of media was removed and fresh media added at 3 day intervals. Once cell numbers were within the 1000–5000 per well range, hybridoma supernatants were tested for reactivity to CTLA4Ig and for a lack of reactivity to CD4Ig by ELISA as described in section (b) above. Hybridoma supernatants were used undiluted in the ELISA (50 μl/well).

Hybridomas from positive wells were repetitively cloned by limiting dilution in the presence of irradiated mouse thymocyte feeder layers. A hybridoma line secreting a monoclonal antibody, termed antibody 9H10, was selected by the following criteria:

1) reactivity against CTLA-4Ig but not CD4Ig in ELISAs; 2) the ability to block CTLA-4Ig binding to B7 transfectants; 3) the ability to stain activated T cells but not freshly isolated T cells; and 4) the ability to stain a CTLA-4 transfectant but not control transfectants.

The ability of antibody 9H10 to block CTLA4Ig binding to B7 transfectants was demonstrated as follows. Approximately 10 μl of mAb 9H10 was incubated at 22° C. for 30 min with 1 μg of CTLA4Ig fusion protein in a final volume of 50 μl of a solution comprising PBS. To this mixture was added $2\times10^5$ B7-EL-4 cells, suspended in 10 μl ice-cold PBS containing 1% calf serum and 0.05% sodium azide. B7-EL-4 cells are the C57BL/6-derived EL4 thymoma cell line transfected with an expression vector encoding the mouse B7 cell surface protein, as described in Townsend et al. Cancer Res. 54:6477–83 (1994).

The resulting mixture was then incubated on ice for 30 minutes, followed by two washes with 4 ml/wash of PBS containing 1% calf serum and 0.05% sodium azide. The cells were then stained with fluorescein isothiocynate (FITC)-conjugated anti-human IgG (Caltag, South San Francisco, Calif.). As a negative control for this experiment, the CTLA-4Ig fusion protein was incubated with either a control hamster IgG or the EL-4 parent cell line. The cells were analyzed on a FACScan (BectonDickinson, Mountain View, Calif.); the LYSIS II program (Becton Dickinson) was used to electronically gate on relevant populations. In most experiments, 10,000 live gated events were collected for analysis. The results showed that the 9H10 antibody blocked CTLA-4 binding to B7-EL-4 cells.

The ability of the 9H10 antibody to stain activated T cells but not freshly isolated T cells was demonstrated as follows. Fresh and activated splenocytes were generated. Spleens from 4–6 week BALB/c mice were harvested and minced, and suspensions were treated with hemolytic Gey's solution to remove the red blood cells, a standard technique in the art [Mishell and Shiigi, Selected Methods in Cellular Immunology, W. H. Freeman and Co., San Francisco (1980) pp.23–24]. The cells were cultured in RPMI containing 10% fetal calf serum, with soluble anti-CD-3 antibody at 10 μg/ml added to activate one portion of the cell population. The other portion of the splenocytes was not treated with anti-CD3 and represents fresh (but not activated splenocytes). The two cell populations were then stained with either 1) a combination of FITC-conjugated 9H10 (the anti-CTLA-4 antibody; 5 μg of antibody) and PE-conjugated Thy1.2 or 2) a combination of FITC-conjugated hamster Ig and PE-conjugated Thy1.2. The data were analyzed on a FACScan and was electronically gated for Thy1.2 positive cells to analyze only the relevant T cell population. The results of this experiment demonstrated that the 9H10 antibody stained activated (i.e., CTLA-4 expressing) but not freshly isolated T cells.

The ability of the 9H10 antibody to stain a CTLA-4 transfectant but not control transfectants was demonstrated as follows. A parent CHO (Chinese Hamster Ovary, CHO-K1 cells) cell line (ATCC CCL 61) was transfected with pSRlneo.CTLA-4. pSRlneo.CTLA-4 contains the entire 1.9 kb cDNA encoding the mouse CTLA-4 protein [Brunet et al., Nature 328:267 (1987)] inserted into the pSRlneo expression vector. Cells transfected with the pSRlneo.CTLA vector express the mouse CTLA-4 protein on the cell surface.

The parent (i.e., CHO-K1 cells) and transfected cells were stained either 1) a combination of FITC-conjugated 9H10 (the anti-CTLA-4 antibody; 5 μg of antibody) and PE-conjugated Thy1.2 or 2) a combination of FITC-conjugated hamster Ig and PE-conjugated Thy1.2. The data was electronically gated for Thy1.2 positive cells to analyze only the relevant T cell population. The results of this experiment demonstrated that the 9H10 antibody stains CTLA-4 transfectants but not control transfectants.

The above results demonstrated that the 9H10 monoclonal antibody reacts specifically with the mouse CTLA-4 protein.

EXAMPLE 2

Anti-CTLA-4 Monoclonal Antibodies Cause Rejection of V51BLim1O Tumors in Mice

The anti-mouse CTLA-4 monoclonal antibody, 9H10, was used to treat mice that received injections of a colon carcinoma cell line. The injection of the 9H10 mAb along with V51BLim 1O tumor cells resulted in the complete rejection of the tumor cells in the experimental animals. In contrast, mice injected with an anti-CD28 mAb and V51BLim10 cells or mice injected with V51BLim10 cells alone both developed tumors which exhibited a steady increase in average tumor size over a period of four weeks.

a) Generation of the V51BLim10 Cell Line

The V51BLim10 cell line was generated by transfection of the SRlneo expression vector into the 51BLim10 cell line. The 51BLim cell line is a colon carcinoma cell line that provides an accurate animal model for colon cancer metastasis in humans. Bresalier, et al., Cancer Res. 47:1398 (1987).

The V51BLim10 cell line used in the present experiments was generated as follows. The murine colon cancer cell line 51B established by Corbett et al., Cancer Res. 35:2434–9

(1975) was injected into the cecal wall of BALB/c mice; the resulting colonic tumors were found to spontaneously metastasize to the liver in a minority of the injected mice. Bresalier et al, Cancer Res. 47:1398 (1987). Tumor cell lines having progressively increased metastatic activity were developed by collecting cells from the original metastases, which were then used for successive reinjection into the ceca of additional mice. These cell lines were termed 51BLim-1 through 51BLim-5 where the number following the dash refers to the number of metastatic cycles.

A 51 B metastatic derivative obtained from Dr. Warren at the University of California San Francisco was designated 51BLim10; the 51BLim10 cell line corresponds to the 51BLiM5 cell line described by Bresalier, et al., Cancer Res. 47:1398 (1987).

The SRlneo expression vector was transfected into the 51 BLiM-10 cell line to generate the V51BLim10 cell as described [Townsend et al. Cancer Res. 54:6477–83 (1994)]. The SRlneo expression vector (obtained from L. Lanier at DNAX Research Institute of Molecular and Cellular Biology, Palo Alto, Calif.) allows the expression of a gene of interest under the transcriptional control of the HTLV-1 LTR. The SRlneo vector also contains the neo gene under the transcriptional control of the S40 promoter/enhancer. The presence of the neo gene allows for the selection of transfected cells containing the SRlneo vector.

The SRlneo expression vector was transfected into 51 BLiM-10 cells by electroporation using a BTX T 800 electroporator (BTX, Inc., San Diego, Calif.).

Five pulses for 99 $\mu$s each at 450 or 600 V were applied. The electroporation was carried out in a final reaction volume of 750 $\mu$l of a solution comprising 270 mM sucrose, 7 mM NaPO$_4$ (pH 7.4), 1 mM MgCl$_2$, $5\times10^6$ 51B LiM-10 cells and 50 $\mu$g of the SRlneo expression vector. Following electroporation, the cells were cultured for 24 hours in complete medium [Eagle's MEM (Univ. of Calif. at San Francisco Cell Culture Facility, San Francisco, Calif.) supplemented with 10% FCS (Sigma), nonessential amino acids, MEM vitamin solution, L-glutamine, sodium pyruvate, gentamicin (all from Irvine Scientific, Santa Ana, Calif.) and 7.5% sodium bicarbonate (Sigma)] at 37° C. Selection medium [complete medium containing 1 mg/ml Geneticin (G418 sulfate, GIBCO, Grand Island, N.Y.)]. After 14 days of culture in the selection medium, drug resistant cells were pooled and used in subsequent experiments as a polyclonal population referred to as V51BLim10.

V51BLim10 tumor cells were maintained in Eagle's MEM (Univ. of Calif. at San Francisco Cell Culture Facility, San Francisco, Calif.) supplemented with 10% FCS (Sigma), non-essential amino acids, MEM vitamin solution, L-glutamine, sodium pyruvate, gentamicin, penicillin-streptomycin (all from Irvine Scientific, Santa Ana, Calif.) and 1 mg/ml Geneticin. Cell cultures were established from low passage (i.e, less than 10 passages) frozen aliquots and maintained in culture for no more than 30 days prior to use.

V51BLim10 cells and the parental 51BLim10 cells were found to exhibit similar in vitro and in vivo growth rates. The expression of the neomycin resistance gene in the V51BLim10 cells and a variety of other tumor cell lines has had no effect on the tumorigenicity or growth rate of tumors from the injected cells.

b) Injection of Mice with V51BLim10 Tumor Cells and Monoclonal Antibodies.

The V51BLim10 tumor cells were harvested from tissue culture plates with trypsin-EDTA (Sigma), washed three times in serum-free media (Eagle's MEM) and suspended at a concentration of $2\times10^7$ cells/ml.

The mice used in this experiment were 6–8 week old female BALB/c mice (Charles River Laboratories, Wilmington, Mass.). Groups of five mice were anesthetized by methoxyflurane inhalation, ear notched for identification, and injected with 200 $\mu$l of the V51BLim10 tumor cell suspension ($4\times10^6$) subcutaneously in the left flank. Treated groups received 100 $\mu$g intraperitoneal injections of the antiCTLA-4 mAb 9H10 described above, or alternatively the anti-CD28 mAb, 37.51, on the same day, and additional 50 $\mu$g i.p. injections on days 3 and 6 following the injection of the tumor cells (designated by the darkened arrows in FIG. 1). The monoclonal anti-CD28, 37.51, is directed against the mouse CD28 protein [Gross et al., J. Immunol. 149:380 (1992)] and served as a negative control.

The mice were monitored for subcutaneous tumor growth and the bisecting diameters of developing tumors were measured with calipers. All of the mice left untreated, or treated with anti-CD28 antibody, developed progressively growing tumors and required euthanasia by 35 days after inoculation. In contrast, all mice treated with anti-CTLA-4 antibody completely rejected their tumors after a short period of limited growth. As shown in FIG. 1A, the average tumor area in mm2 (displayed along the y axis) decreased gradually starting at approximately day 14 post-tumor injection (displayed along the x axis), decreasing to zero at approximately day 24. Anti-CTLA-4 treatment was less effective at smaller tumor doses. FIG. 1B shows the average tumor size in mice injected with $2\times10^6$ tumor cells and treated as described above with anti-CTLA-4 antibody or an irrelevent hamster antibody. Anti-CTLA4 antibody treatment continued to have a dramatic effect on tumor growth, but one mouse developed a tumor quickly, and another much later. FIG. 1C illustrates the individual tumor growth in mice injected with $2\times10^6$ V51BLim10 cells. Three of the mice remained tumor free beyond 80 days. It is clear that CTLA-4 blockade significantly enhanced rejection of the B7 negative tumor cells.

c) Injection of Mice with B7-51BLim10 Tumor Cells and Monoclonal Antibodies. 51BLim10 cells were transfected as described above, with a plasmid containing the gene for murine B7-1, and cloned by limiting dilution. The B7-51BLim10 tumor cells were harvested from tissue culture plates with trypsin-EDTA (Sigma), washed three times in serum-free media (Eagle's MEM) and suspended at a concentration of $2\times10^7$ cells/ml.

The mice used in this experiment were 6–8 week old female BALB/c mice (Charles River Laboratories, Wilmington, Mass.). Groups of five mice were anesthetized by methoxyflurane inhalation, ear notched for identification, and injected with 100 $\mu$l of the B7-51BLim10 tumor cell suspension ($4\times10^6$) subcutaneously in the left flank. Treated groups received 100 $\mu$g intraperitoneal injections of the anti-CTLA-4 mAb 9H10 described above, or alternatively the anti-CD28 mAb, 37.51. Injections of 100, 50 and 50 $\mu$g were given on days 0.3 and 6, respectively (injection days are designated by the darkened arrows in FIG. 2). The monoclonal anti-CD28, 37.51, is directed against the mouse CD28 protein [Gross et al., J. Immunol. 149:380 (1992)] and served as a negative control.

The mice were monitored for subcutaneous tumor growth and the bisecting diameters of developing tumors were measured with calipers. The data from this experiment is shown in FIG. 2. Treatment with anti-CTLA-4 antibodies inhibited B7-51BLim10 tumor growth as compared to the anti-CD28 and control groups. All mice in the untreated and anti-CD28 treated groups developed small tumors that grew progressively for five to ten days and then ultimately regressed in eight of the ten mice by about day 23 post injection. The two small tumors that did not regress remained static for over 90 days. In contrast, 3 of the 5 mice treated with anti-CTLA-4 antibody developed very small tumors, and all of these regressed completely by day 17.

d) Anti-CTLA-4 induced rejection of V51BLim10 tumor cells results in protection against subsequent challenge with wild-type colon carcinoma cells.

Five anti-CTLA-4 treated mice that had completely rejected V51BLim10 tumor cells were rechallenged 70 days later with $4 \times 10^6$ wild-type 51BLim10 tumor cells injected sub-cutaneously in the opposite flank. Five naive mice were also injected as controls. Tumor diameters were measured and reported as described. Prior tumor rejection resulted in significant protection against secondary challenge as compared to naive controls. All control mice developed progressively growing tumors, developed massive tumor burdens, and were euthanized on day 35 post-inoculation. 3 of 5 previously immunized mice remained tumor free 70 days after challenge. Only one of the previously immunized mice had a detectable tumor by day 14, and growth of this tumor was very slow. Utimately, two more tumors developed in the immunized mice 42 days after challenge. The data is shown in FIG. 3. These results demonstrated that tumor rejection mediated by CTLA-4 blockade resulted in immunologic memory.

e) Anti-CTLA-4 treatment reduces the growth of established tumors.

Groups of mice were injected s.c. with $2 \times 10^6$ 51BLim10 tumor cells. Control animals (n=10) were injected i.p. with 100 µg irrelevant hamster antibody on days 0, 3, 6 and 9, as indicated by the upward pointing arrows in FIG. 4. One anti-CTLA-4 treatment group received i.p. injections on the same days. The other treated mice (n=5) were given i.p. injections of anti-CTLA-4 antibody beginning on day 7 and subsequently on days 10, 13 and 16 (downward pointing arrows). Data is shown in FIG. 4. Mice treated with anti-CTLA-4 antibodies at either time point had significantly reduced tumor growth compared to untreated controls. Delaying treatment appeared to be more effective, with 2 of 5 mice remaining tumor free beyond thirty days after inoculation.

f) Anti-CTLA-4 treatment reduces the growth of the murine fibrosarcoma SA 1N.

The effects of anti-CTLA-4 treatment were not limited to carcinoma cell lines. Similar results were obtained with a rapidly growing fibrosarcoma cell line of A/JCr mice. Groups of mice were injected s.c. in the flank with a suspension of $1 \times 10^6$ SA1N fibrosarcoma cells. Treated groups were injected i.p. with 100 µg anti-CTLA-4 or irrelevant hamster control antibody at days 0, 3 and 6, as indicated by the arrows in FIG. 5. All control animals were killed by day 30. Two of five anti-CTLA-4 treated animals remained tumor free at day 55. Data is shown in FIG. 5.

EXAMPLE 3

Anti-CTLA-4 Monoclonal Antibodies Act as an Adjuvant a) Preparation of immunogen DNP-KLH was obtained from Calbiochem (San Diego, Calif.) and was suspended in deionized water at 1 mg/ml, 100 ng/ml or 10 pg/ml. One ml of Freund's Complete Adjuvant (Difco, Mich.) was added to each 1 ml of the DNP-KLH preparations. These were then emulsified in two 5 ml syringes connected by a double-ended luer lock connector by rapid passage through the luer lock, as described in *Current Protocols in Immunology,* Colligan et al., eds., section 2.4.

30 minutes prior to injection of the immunogen, C57Bl/6 mice of 4–6 weeks in age were injected in the peritoneum using a 23 gauge syringe with 200 µg of non-specific control hamster antibody or with 200 µg of anti-CTLA-4 antibody 9H10 (both in 200 µl total volume). The mice were subsequently injected subcutaneously using a 21 gauge syringe at two sites on the back, with 200 µl of the immunogen in the form described above, giving a dose of 100 µg, 10 ng or 1 pg/mouse, respectively. After three days the antibody injections were repeated.

Ten days following the first treatment, the animals were euthanized. Blood was obtained by heart puncture and removed to eppendorf tubes. These samples were allowed to coagulate at 4° C. overnight, and were then centrifuged to obtain sera.

Sera was analyzed for isotype specific antibodies recognizing DNP using a standard isotype ELISA, as described in *Current Protocols in Immunology* (supra.) section 2.1. Briefly, DNP was plated at 100 ng/ml in 50 µl volume in each well of a 96 well Corning modified round-bottom ELISA plate. The wells are blocked using buffers as described. Three-fold serial dilutions of each sera, starting at 1:100 are added to each well. These are incubated for one hour at 25° C., and washed with wash buffer. Isotypes are detected by using mouse specific antibodies as detecting agents at 1 µg/ml in 50 µl of blocking buffer incubated for one hour. The isotype antibodies are biotinylated, and detection is achieved by incubating with avidin-horseradish peroxidase, washing and addition of peroxidase substrate (ABTS, Sigma, Mo.). Stop buffer is added, and the absorbance of each well read with an ELISA reader at a wave length of 490–498 nm within 5–8 min of stopping the reaction.

The results are shown in FIGS. 6A to 6E. Each of the panels illustrates the concentration of a different isotype in the serum sample. The y axis shows the O.D. reading, where an increase in O.D. indicates increased concentration of antibodies in the serum having that isotype. The x axis shows the amount of antigen that was injected, 100 µg, 10 ng or 1 pg per animal, respectively. It can be seen that anti-CTLA-4 antibody increases class switching to IgG1, IgG2a and IgG2b at the higher dose of antigen.

Analysis of T cell function was performed as follows. Lymph node cells were isolated and stimulated in vitro for 72 hours with KLH. The axillary, inguinal, mesenteric, brachial, cervical and popliteal lymph nodes were removed to a dish containing RPMI-complete (10% FCS (Hyclone, Mont.), 2 mM glutamine, 50 µM β-mercaptoethanol, 50 µg/ml gentamycin). The lymph nodes were minced to obtain single cell suspensions, filtered through a nytex mesh to remove particulate, and counted using a hemocytometer. Cells were plated in 150 µl of RPMI-complete in 96 well round bottom cluster plates at either $5 \times 10^5$, $2.5 \times 10^5$, or $1.25 \times 10^5$ cells/well. KLH solutions in RPMI-complete were added to final concentrations of 100, 10, 1 or 0 µg/ml and the plates were incubated at 37° C. for 64 hours in humidified incubators with 5% CO$_2$. After 64 hours, 20 µl of RPMI-complete containing 1 µCi of $^3$H-thymidine was added to each well, and the plates were incubated an additional eight hours. At this time, cultures were harvested onto glass fiber filters using an Inotech 96 well harvester. Filters were dried and counted using a Packard Matrix counter. Each condition was performed in triplicate, and data represents the mean of triplicate values.

The results are shown in FIGS. 7A to 7B. The top row shows a constant number of cells ($5 \times 10^5$ cells), with varying concentrations of antigen (shown on the x axis). The y axis shows incorporation of $^3$H-thymidine, a measure of cell proliferation. The lower panel shows a constant antigen concentration (10 μg/ml), with varying numbers of cells (shown on the x axis). The data indicates that CTLA-4 blockade strongly upregulates the T cell response to the higher doses of antigen.

EXAMPLE 4

Generation of Antibodies Directed Against Human CTLA-4 Proteins

Anti-human CTLA-4 antibodies are generated as follows.
a) Human CTLA-4 Proteins for Immunization of Host Animals Immunogens comprising human CTLA-4 proteins contain all or a portion of the extracellular domain of the human CTLA-4 protein. The extracellular domain of the human CTLA-4 protein comprises amino acid residues 38-161, as listed in the database references.

The human CTLA-4 immunogen comprises the entire human CTLA-4 protein or a fusion protein comprising the extracellular domain of human CTLA-4 and a fusion partner. The immunogen comprises the entire human CTLA-4 protein inserted into the membrane of a cell; the cell expressing human CTLA-4 on the surface is used to immunize a host animal.

Immunogens comprising portions of the human CTLA-4 protein are generated using the PCR to amplify DNA sequences encoding the human CTLA-4 protein from mRNA from H38 cells, an HTLV II-associated leukemia line (R. Gallo, National Cancer Institute). The mRNA is reverse transcribed to generate first strand cDNA. The cDNA is then amplified. These sequences are linked to sequences that encode a fusion partner, as described in Linsley et al. [*J. Exp. Med.* 174:561 (19991)]. The expression vector encodes a fusion protein termed CTLA-4Ig, which comprises (from amino- to carboxy-termini) the signal peptide from oncostatin M, the extracellular domain of human CTLA-4 and the H, CH2 and CH3 domains of human IgG1. The signal peptide from oncostatin M is used in place of the naturally occurring human CTLA-4 signal peptide. The cysteine residues found in the wild-type hinge domain of the human IgG1 molecule were mutated to serines in the construction of the vector encoding the CTLA-4Ig protein (Linsley et al., supra).

b) Immunization of Host Animals With Human CTLA-4 Proteins

To immunize animals with immunogens comprising human CTLA-4 proteins, non-human host animals are employed. The immunogen comprising a human CTLA-4/IgG fusion protein (e.g., CTLA-4Ig), is used to coat heat-killed Staphylococcus A (StaphA) bacteria cells as described in Example 1b. Six week old BALB/c mice are injected in the footpad with 50 μl (packed volume) of heat-killed StaphA bacteria coated with approximately 100 μg of CTLA-4Ig suspended in 0.2 ml of PBS.

A total of five injections are given per mouse. On the day of the final boost and prior to the injection, approximately 100 μl of serum is obtained by intraocular bleeding as described in Example 1b. The serum is analyzed in companion to serum obtained by the identical methodology prior to the first injection (ie., pre-immune serum).

A human CTLA-4Ig binding ELISA is utilized to demonstrate the presence of antibody that recognizes the human CTLA-4Ig fusion protein in the post-immunization bleed. The human CTLA-4Ig binding ELISA is conducted as described above in Example 1b with the exception that the ELISA plates are coated with human CTLA-4 protein.

The serum and lymph nodes of the immunized mice containing antibody that recognizes the human CTLA-4Ig fusion protein in the post-immunization bleed at serum dilutions 1000-fold greater than the dilution at which background could be detected are collected. Lymphocytes are prepared from draining lymph nodes in the immunized mice and are then used for the generation of monoclonal antibodies directed against the human CTLA-4 protein as described above in Example 1c.

Immunogens comprising transformed cells expressing the human CTLA-4 protein on the cell surface are prepared as follows. Expression vectors encoding the entire human CTLA-4 protein are used to transfect the mouse lymphoma cell line EL4 (ATCC TIB 39). Transfected EL4 cells are injected into mice using $1\times10^6$ to $1\times10^7$ transfected cells/injection. The transfected cells are injected in a solution comprising PBS. The mice may be injected either i.p. or in the hind footpad. When i.p. injections are given, a total of approximately 4 injections are administered. When the footpad is used as the site of injection, a total of approximately 5 injections are administered. Serum is collected from the immunized animals and tested for the presence of antibodies directed against the human CTLA-4 protein using an ELISA as described in Example 1b, with the exception that the plates are coated with human CTLA-4 proteins.

c) Isolation of Hybridoma Lines Secreting Anti-Human CTLA-4 Antibodies

Lymphocytes are isolated from draining lymph nodes or the spleens of animals immunized with the human CTLA-4 immunogen and fused to P3X3.Ag8.653 cells to generate hybridoma cell lines using the PEG fusion protocol described in Example 1c. Culture supernatant from wells containing 1000–5000 cells/well are tested for reactivity to human CTLA-4 and for lack of reactivity to a non-CTLA-4 protein such as human CD4 using an ELISA assay.

Hybridomas from positive wells are repetitively cloned by limiting dilution as described in Example 1c. Hybridoma lines secreting monoclonal antibodies that are reactive against human CTLA-4 proteins but not irrelevant human proteins (e.g., human CD4), and that have the ability to stain cells human CTLA4 transfectants but not control transfectants are selected for production of anti-human CTLA-4 monoclonal antibodies.

EXAMPLE 5

Ex Vivo Stimulation of Tumor Infiltrating Lymphocytes (TILs)

Host cells are stimulated ex vivo, allowing them to differentiate into tumor-specific immune effector cells. The cells are then reintroduced into the same host to mediate anticancer therapeutic effects.

a) Isolation of Tumor-Infiltrating Lymphocytes (TILs)

Tumor-infiltrating lymphocytes are obtained using standard techniques. Solid tumors (freshly resected or cryopreserved) are dispersed into single cell suspensions by overnight enzymatic digestion [e.g., stirring overnight at room temperature in RPMI 1640 medium containing 0.01% hyaluronidase type V, 0.002% DNAse type I, 0.1% collagenase type IV (Sigma, St. Louis), and antibiotics]. Tumor suspensions are then passed over Ficoll-Hypaque gradients (Lymphocyte Separation Medium, Organon Teknika Corp., Durham, N.C.). The gradient interfaces contain viable tumor cells and mononuclear cells are washed, adjusted to a total cell concentration of 2.5 to $5.0\times10^5$ cells/ml and cultured in complete medium. Complete medium comprises RPMI 1640 with 10% heat-inactivated type-compatible human serum, penicillin 50 IU/ml and streptomycin 50 μg/ml (Biofluids, Rockville, Md.), gentamicin 50 μg/ml (GIBCO Laboratories, Chagrin Falls, Ohio), amphotericin 250 ng/ml (Funglzone, Squibb, Flow Laboratories, McLean, Va.), HEPES buffer 10 mM (Biofluids), and L-glutamine 2 mM (MA Bioproducts, Walkersville, Md.). Conditioned medium from 3- to 4-day autologous or allogeneic lymphokine-activated killer (LAK) cell cultures (see below) is added at a final concentration of 20% (v/v). Recombinant IL-2 is added at a final concentration of 1000 U/ml.

Cultures are maintained at 37° C. in a 5% $CO_2$-humidified atmosphere. Cultures are fed weekly by harvesting, pelletting and resuspending cells at $2.5 \times 10^6$ cells/ml in fresh medium. Over an initial period (e.g., 2 to 3 weeks) of culture, the lymphocytes selectively proliferate, while the remaining tumor cells typically disappear completely.

To make LAK cell cultures, peripheral blood lymphocytes (PBL) are obtained from patients or normal donors. After passage over Ficoll-Hypaque gradients, cells are cultured at a concentration of $1 \times 10^6$/ml in RPMI 1640 medium with 2% human serum, antibiotics, glutamine, and HEPES buffer. Recombinant IL-2 is added at 1000 U/ml. Cultures are maintained for 3 to 7 days in a humidified 5% CO2 atmosphere at 37° b) Ex Vivo Stimulation of TILs $4 \times 10^6$ cells, in 2 ml of culture medium containing the anti-CTLA-4 mAbs, are incubated in a well of 24-well plates at 37° C. in a 5% $CO_2$ atmosphere for 2 days. The culture medium comprises RPMI 1640 medium supplemented with 10% heat inactivated fetal calf serum, 0.1 mM nonessential amino acids, 1 μM sodium pyruvate, 2 mM freshly prepared L-glutamine, 100 μg/ml streptomycin, 100 U/ml penicillin, 50 11g/ml gentamicin, 0.5 μg/ml fungizone (all from GIBCO, Grand Island, N.Y.) and $5 \times 10^{-5}$M 2-ME (Sigma). The cells are harvested and washed.

The initially stimulated cells are further cultured at $3 \times 10^5$/ well in 2 ml of culture media with recombinant human IL-2 (available from Chiron Corp., Emeryville, Calif.; specific activity of 6 to $8 \times 10^6$ U/mg protein; units equivalent to 2-3 International U). After 3 days incubation in IL-2, the cells are collected, washed, counted to determine the degree of proliferation, and resuspended in media suitable for intravenous (i.v.) administration (e.g. physiological buffered saline solutions). Bacterial cultures are performed to determine the existence of bacterial contamination prior to reinfusion of the activated cells.

After the activated TILs have been resuspended in a media suitable for injection, IV access is obtained in the host and the cell suspension is infused. Optionally, the host is treated with agents to promote the in vivo function and survival of the stimulated cells (e.g. IL-2).

EXAMPLE 6

In this study we investigated the effect of CD28 and CTLA-4 signals on the responses of T cell populations in response to the superantigen Staphylococcus enterotoxin B (SEB) in vitro and in vivo. The results indicate that CD28 provides an important costimulus for the SEB response in vitro and that signals through CTLA-4 inhibit the response. In vivo, blockade of CD28 by FAb fragments or intact antibodies have the opposite effects upon Vβ8+ expansion to a similar blockade with anti-CTLA-4 FAb fragments or intact antibodies. Analysis of the kinetics of the expansion imply that signals through CD28 promote T cell expansion, whereas an opposing signal through CTLA-4 functions during T cell expansion to attenuate the magnitude of the response to SEB.

Methods

Mice. BALB/c mice were purchased at four to five weeks of age from Charles River and were used within three weeks.

Antibodies and Reagents. Hamster anti-mouse CD28 from clone 37.N.51.1 (Gross et al. (1992) *J. Immunol.* 149:380), hamster anti-mouse CTLA-4 from clone 9H10.11D3 (Krummel and Allison (1995) *J. Exp. Med.* 182:459) hamster anti-mouse B7-1 from clone 1610.A (Razi-Wolf et al. (1992) *J. Exp. Med.* 89:4210), rat anti-mouse B7-2 (from clone GL-1 (Hathcock et al. (1993) *Science* 262:905) and irrelevant hamster IgG from clone F560.31 were purified from ascities fluid in our facility. FAb fragments were obtained by digestion with immobilized papain (Pierce, Rockford Ill.) by standard methodology and undigested antibody was removed by Protein A adsorption. All FAb fragments were analyzed by SDS-PAGE prior to use. Purity of anti-CD28 FAbs was further tested in functional assays for the ability to block T cell proliferation in an allo-MLR. Anti-$V_β8.1,8.2$ FITC (clone MR5-2) was obtained from Pharmingen (San Diego, Calif.).

In Vitro Assays. Spleens obtained from naive animals were minced to obtain suspensions and RBCs were lysed by hypotonic treatment with Geys solution followed by two washes with PBS. $2 \times 10^5$ splenocytes were plated in 200 μl RPMI (containing 10% FCS, 50 μM β-mercaptoethanol, 2 mM glutamine, and 50 μg/ml gentamycin) in 96 well round bottom plates. SEB was added at the indicated concentrations. Where indicated, anti-CD28 was added at a 1:1000 dilution of ascites, anti-B7-1 was added at 5 μg/ml and anti-B7-2 was added at 20 μg/ml, and equal quantities of non-specific control antibody 560.31 were added. For FAb experiments, anti-CD28, anti-CTLA-4 or control FAb fragments were added at 100 μg/ml. Cultures were incubated for 60 hours at 37° C., pulsed with 1 μCi of $^3$H thymidine and allowed to incubate for a further 12 hours prior to harvesting.

In Vivo SEB Responses. Mice were injected intraperitoneally with 200 μl of PBS containing, where indicated, 200 μg of antibody. After 1–2 hours, mice were injected intravenously with 50 μg per animal of SEB (Toxin Technologies, Sarasota, Fla.) in PBS or PBS alone in 100 μl total volume.

Flow Cytometry. To evaluate the population of $V_β8$ expressing cells, spleens were minced to obtain suspensions and RBCs were lysed using a hypotonic Geys solution. The resulting cells were then resuspended in 5 ml of RPMI-10%FCS and triplicate aliquots were counted using a hemocytometer. Standard error for this was routinely within 10% of the mean. For staining, aliquots were washed once in PBS/1%FCS with 0.01% $NaN_3$ and resuspended in PBS/FCS at a concentration of $10^6$ cells/50 μl. Antibodies were added and incubated on ice for 30 minutes. Cells were washed and subsequently analyzed using a FACScan cytometer utilizing the Lysisll software (Becton-Dickinson, Mountain View, Calif.). 10,000 live gated events were analyzed for the percentage expressing $V_β8^+$ and was used to obtain the total number of $V_β8$ cells by applying the formula: #Vβ8=Total Cell Yield×%Vβ8 in sample.

Results

Role of Costimulation in SEB Mediated Proliferation In vitro. The proliferative response of splenocytes from BALB/c mice to SEB was investigated to determine the role of B7/CD28 interactions. As SEB was added to splenocytes, dose-dependent proliferation was observed in the cultures. B7 molecules on cells in these cultures appear to supply costimulation, since addition of anti-B7-1/B7-2 antibodies significantly inhibited the response. Further, increased CD28 signaling via anti-CD28 antibodies enhanced the proliferative response. This increase may have been mediated by immobilization of antibody on FcR+ B cells or by the formation of antibody microaggregates. Interestingly, the addition of anti-CD28 and anti-B7-1/B7-2 induced a slight but reproducible increase in proliferation compared to anti-CD28 by itself, suggesting that another B7 ligand besides CD28 (i.e. CTLA-4) might be important in downregulating the response of T cells to SEB.

To address the relative contibutions of CD28 and CTLA-4 on the T cell response, antibody Fab fragments specific for these molecules were added to SEB stimulated cultures. Addition of CD28 FAbs inhibited the SEB dependent proliferation. The magnitude of the CD28 FAb blockade is similar to that observed using anti-B71/2 antibodies, implicating CD28/B7 interactions in providing some costimulation for proliferation in the control cultures. However, there was a two to three-fold augmentation of proliferation in the presence of CTLA-4 FAb, implying that CTLA-4 signals plays an important part in regulating the response. This further emphasizes that B7 molecules on APC create an interplay of amplifying signals through CD28 and attenuating signals through CTLA-4.

CD28 and CTLA-4 Signals Have Opposing Effects on In vivo Expansion of $V_\beta 8^+$ T cells. The effects of anti-CD28 and anti-CTLA-4 antibody treatment on the T cell response to SEB was examined. T cell expansion to superantigens in vivo typically occurs within 2–3 days post-injection. 60 hours was chosen as a convenient timepoint to initially analyze the affects of anti-CD-28 and anti-CTLA-4 upon the response. Animals were injected with PBS or SEB and the relevant mAbs or FAb fragments. After 60 hours, the total number of $V_\beta 8$-bearing TCRs was determined by counting the spleen cellularity and antibody staining samples to determine the percentage of Vβ8+ cells. The total number of Vβ8-bearing cells isolated from the spleen of animals injected with SEB and control antibodies was approximately 2–3 times the number present in control (PBS) injected animals. In contrast, the injection of increasing doses of anti-CD28 in addition to SEB decreased the number of Vβ8-bearing cells observed at this time point. The injection of 5 µg of anti-CD28 modestly decreased the number of recovered Vβ8 and both 20 µg and 200 µg injections gave roughly identical two-fold reductions. To address the discrepancy of this result and in vitro results showing anti-CD28-mediated amplification of T cell responses, daily doses of FAb fragments of CD28 antibody were injected during the SEB response. In a similar manner to intact antibodies, these FAbs blocked the expansion of Vβ8+ cells to SEB in a dose-dependent manner. The inhibitory effects of intact antibodies was similar to that observed using FAbs, implying that anti-CD28 antibodies and FAb fragments in vivo both interfere with B7/CD28 signals. This may be the result of inefficient signaling by bivalent antibody and competition with native ligand by both antibody and FAb fragments.

To compare the effects of CD28 versus CTLA-4, anti-CTLA-4 antibodies were co-injected with SEB. In contrast to what was observed with anti-CD28 treatment, administration of anti-CTLA-4 resulted in a dose-dependent increase in accumulation of splenic Vβ8+ cells. The highest dose of anti-CTLA-4 produced a 2–3 fold increase in the number of Vβ8+ cells over that observed with SEB alone. The daily injection of anti-CTLA-4 FAb fragements also gave sizable increases in the number of Vβ8+ cells detected at 60 hours. The fact that both intact anti-CTLA-4 and its monovalent FAb fragment produced the same result suggest that under these conditions both forms of the antibody were blocking CTLA-4/B7 interactions. Further, the observation that an increase in Vβ8+ cells was observed under these conditions is consistent with the notion that the antibodies block an inhibitory signal.

Kinetic Analysis of SEB Responsive Populations. A kinetic analysis was performed to address whether CD28 and CTLA-4 affect the magnitude of the response or its timing. An antibody dose of 200 µg/injection was utilized, as this dose was in the range required for saturation of CD28, as determined by flow cytometry. The response to SEB and control antibodies was as expected; the expansion phase peaked at day 3, followed by a steady decline. In contrast, mice treated with anti-CD28 and SEB showed only minimal expansion with the peak at 72 hours being less than a third of control levels. However, these cells appear to have undergone an expansion and the cell numbers decay over the subsequent seven days.

Mice receiving SEB and anti-CTLA-4 mAbs showed increased cell numbers relative to control antibody treated animals throughout the time course of the experiment. The number of cells increased dramatically over the first three days with rapidly decreasing cell numbers reaching levels similar to control/SEB injected animals by day 10. At the peak of the response, CTLA-4 treated animals had approximately twice as many Vβ8+ T cells relative to control antibody treated animals. Finally, to address whether CTLA-4 or CD28 present a dominant signal, both antibodies were added simultaneously. Throughout the time course, this treatment produced results identical to those obtained with animals treated with anti-CD28 alone.

B7/CD28/CTLA-4 Interactions Are Important for Regulating the SEB Response In Vitro. The data presented here suggests an important role for costimulatory signals in the response of murine T cells to the superantigen SEB. Endogenous interactions of B7-1/B7-2 with CD28 are important for promoting proliferation since blocking with either anti-B7-1/2 antibodies or anti-CD28 FAb fragments drastically reduced SEB-induced proliferation. In contrast, engagement of CD28 by intact anti-CD28 antibodies increases proliferation above the threshold provided by APC. This increase is probably due to microaggregation or FcR-mediated aggregation of anti-CD28 antibodies leading to efficient crosslinking of CD28.

In contrast to CD28, CTLA-4 interactions with B7 molecules dampens the T cell response to SEB. The observation that anti-CTLA-4 FAb fragments enhance proliferation indicates that CTLA4/B7 interactions inhibit proliferative response of T cells to SEB. Further, anti-B7-1/2 antibodies augment proliferation in the presence of optimal stimulation with CD28 antibodies, providing additional support for the notion that the inhibitory signals are mediated through CTLA-4-B7 interactions.

CD28 and CTLA-4 Have Opposing Effects on the SEB Induced Expansion of Tcells In vivo. Manipulation of costimulation in SEB treated mice by directly interfering with signals transduced through CD28 or CTLA-4 have opposite effects on the expansion of the Vβ8+ T cells. This result supports previous in vitro data which suggests that these molecules might compete to determine the proliferative outcome in the presence of a fixed level of TCR signal. There appears to be a requirement for CD28 signals for optimum responses to SEB; blocking with anti-CD28 FAb fragments or intact anti-CD28 antibodies effectively diminishes the proliferative expansion. The observation that CTLA-4 blockade similarly allows increased expansion of responsive cells further supports a similarity in costimulation requirements for superantigen and peptide antigen responses in vivo. Further, the kinetic analysis implies that competition between CD28 and CTLA-4 for B7-molecules determines a very early parameter of the T cell response; in this experiment a CTLA-4-dependent change in expansion occurred within the first two days. While it is clear that CTLA-4 blockade increases the response to SEB when CD28 engagement is allowed, it has no effect upon the residual proliferation when CD28 is blocked.

The data demonstrate that CTLA-4 plays a role in dampening the response to SEB by opposing the effects of CD28. Although this may represent a mechanism for T cell tolerance, the inhibition may also be involved in altering phenotype. For example, signals generated by B7/CTLA-4 signals could induce memory cells or alternative lymphokine expression and effector function.

EXAMPLE 7

Kinetic analysis of the effects of CTLA-4 ligation on proliferation, IL-2 production, cell death, cell cycle progression, and the appearance of T cell activation markers.

Materials and Methods

Antibodies and Reagents: Antibodies used for activation were: anti-CD3 hybridoma 500A2 (Allison et al. (1987) in *The T Cell Receptor*, UCLA Symposia on Molecular and Cellular Biology, New Series. Alan R. Liss, Inc., New York. 33–45), anti-CD28 hybridoma 37.N.51.1 (Gross et al., supra.), anti-CTLA-4 hybridoma 9H10.11G3 (Krummel et al., supra.), and anti-V$\alpha$3 hybridoma 536 (Havran et al. (1989) *P.N.A.S.* 86:4185–4189). CTLA-4Ig is described in Lane et al. (1994) *Immunol.* 80:56–61). APC and CD8 depletion was achieved using anti-Class II MHC hybridomas 28-16-8s (Ozato and Sachs (1981) *J. Immunol.* 126:317–323) and BP107 (Symington and Sprent (1981) *Immunogenetics* 14:53–61), and anti-CD8 antibodies hybridoma 3.155 (Sarmiento et al. (1980) *J. Immunol.* 125:2665–2672). Sulfate polystyrene latex microspheres of 5 $\mu$M±0.1 $\mu$M mean diameter were obtained from Interfacial Dynamics Corp. (Portland, Oreg.).

Preparation of CD4+ T Lymphocytes: Lymph node cells were isolated from 6–8 week old BALB/c mice obtained from NCI (Bethesda, Md.). Isolated lymphocytes were obtained by mincing of tissue and filtration of the resulting suspension through nytex. Enriched CD4+ T cell preparations were obtained by treatment with complement, anti-Class II antibodies, and anti-CD8 antibodies. Typical preparations were 95% CD4+ with less than 0.75% B220 positive cells.

Activation of CD4+ T cells Using Immobilized anti-CD3: Round bottom 96 well plates were coated with anti-CD3 at 0.1 $\mu$g/ml in 50 volumes for 2 hours at 37° C., then washed extensively and blocked for 30 minutes at 37° C. with complete RPMI-1640 (containing 10% FCS, 50 $\mu$M $\beta$-mercaptoethanol, 2 mM glutamine, and 50 $\mu$g/ml gentamycin). T cells were added at 1×10$^5$ per well in 200 $\mu$l of complete RPMI-1640 and all cultures were incubated at 37° C. in 5% CO$_2$. Where indicated anti-CD28 was added at 10 $\mu$g/ml, CTLA-4Ig was added at 5 $\mu$g/ml, and control or anti-CTLA-4 FAb fragments were added at 50 $\mu$g/ml. Twelve hours prior to harvest, wells were pulsed with 20 $\mu$l of complete RPMI containing 1 $\mu$Ci of $^3$H thymidine. Plates were harvested to glass filter mats and $^3$H incorporation was measured using a gas-phase counter (Packard, Meriden, Conn.).

Activation of T cells Using Latex Microspheres: Latex microspheres (beads) were coated as described in Krummel et al. (1995). Briefly, 1×10$^7$ beads/ml were suspended in PBS with the indicated antibodies and incubated for 1.5 hr at 37° C., followed by washing with PBS and blocking with 10% FCS. Anti-CD3 was added at 0.5 $\mu$g/ml, anti-CD28 was added at 1 $\mu$g/ml, anti-CTLA-4 was added at 4 $\mu$g/ml, and binding solutions were normalized with control antibody 536 to maintain a constant total antibody concentration of 6 $\mu$g/ml during binding. T cells (1×10$^5$/200 $\mu$l) were cultured with 1×10$^5$ beads in a total volume of 200 $\mu$l/well. Round bottom 96 well plates were used for all assays. Cultures were incubated at 37° C. in 5% CO$_2$ and pulsed with 1 $\mu$Ci of $^3$H-thymidine for the final 12 hours prior to harvesting. The inhibitory action of CTLA-4 appears specific to anti-CTLA-4 antibodies as other T cell binding antibodies including anti-L selectin (Mel-14), anti-Thy1.2 and irrelevant antibodies show either no effect or augmentatory effects when co-immobilized with anti-CD3 and anti-CD28.

Analysis of Cell Viability: T cells were cultured identically as for proliferation assays. Cell viability was assessed by the addition of one tenth volume of 0.4% trypan blue (Sigma, St.Louis, Mo.) and cell numbers determined using a hemocytometer. 10$^{-4}$ ml of each culture was counted from duplicate wells and the value for this volume was multiplied by 2 to obtain a value for the percent of input (50×10$^4$ cells/ml was input). Standard deviations were always less than ten percent.

Cell Cycle Analysis: Propidium iodide analysis of cell cycle status was performed as previously described (Telford et al. (1992) *Cytometry* 13:137–143). Briefly, cells were activated as described using microspheres in 96 well plates. At the indicated times, three identical wells (3×10$^5$ input at the beginning of culture per sample) were harvested, washed in PBS, and fixed with 1.0 ml of 80% ethanol. Cells were incubated on ice for 30 minutes pelleted by centrifugation and resuspended in 0.4 ml of an aqueous solution containing 0.1% Triton X-100, 0.1 mM EDTA, 0.05 mg/ml RNase A (50 U/mg), and 50 $\mu$g/ml propidium iodide. Samples were stored on ice in the dark until analysis and each sample was analyzed at a constant flow rate for two minutes. Data was analyzed using a Coulter EPICS system.

IL-2 Determination An ELISA was utilized to detect IL-2 in cell supernatants. Briefly, capture antibodies were coated at 1 $\mu$g/ml onto Corning (Corning, N.Y.) ELISA plates in Borate Buffer (0.2M Na Borate pH 8.0) for 2 hours at 37° C. These plates were then washed extensively, blocked with 0.4% Gelatin/PBS for 30 minutes and T cell culture supernatants (50 $\mu$l) were added and incubated for 2 hours at 37° C. Plates were again washed and biotinylated detection antibodies were added in PBS/0.5% Tween and incubated for 1 hour at 37° C. Plates were again washed and a 50 $\mu$l of a solution of 1 $\mu$g/ml Streptavidin-HRPO in PBS/Tween was added and incubated for 30 minutes at 37° C. 50 $\mu$l of developing reagent (0.55 mg/ml ABTS (2,2'-Azino-bis(3-ethylbenzthiazoline-6-sulfonic acid) in citrate buffer (0.1M citric acid pH 4.35) was added, incubated at 25° C. for 15 minutes, and absorbance at 405 nm determined. Recombinant IL-2 was obtained from Boerringer Mannheim and was diluted in series to develop a standard curve. Triplicate absorbance values of test samples were thereby converted to lymphokine quantities measured in nanograms per milliliter. Antibodies (capture: JES-6-1A12 and detection: biotinylated JES6-5H4) were obtained from PharMingen (San Diego, Calif.).

Analysis of CD25 and CD69 Expression. 2×10$^5$ cells were suspended in 50 $\mu$l ice-cold PBS/1% Calf Serum/ 0.05% Sodium Azide. Anti-CD25.FITC, anti-CD69, or control RatIgG FITC antibodies were added, incubated on ice for 30 minutes followed by two 4 ml washes in PBS/Calf Serum/NaAzide. 5,000 live gated events were acquired on a Becton-Dickinson FACScan and the LYSIS II program was used to analyze relevant populations.

Results

CTLA-4 Engagement Inhibits Proliferation and IL-2 Production. It was previously shown that soluble antibodies to CTLA-4 or B7 increased thymidine incorporation and IL-2 production by T cells activated by immobilized anti-CD3 and anti-CD28 in standard three day assays. These results indicated that blockade of CTLA-4/B7 interactions between the T cells themselves augmented responses by removing inhibitory signals. Since the cultures were assayed at a single time point it was not possible to determine when in the course of the cultures the effect occurred. A kinetic analysis of the results of CTLA-4/B7 blockade on the proliferation of purified CD4+ T cells is presented in FIG. 8A. Inclusion of either CTLA-4lg or Fab fragments of anti-CTLA-4 to cultures stimulated with anti-CD3 and anti-CD28 resulted in an increase proliferation. The effect was slight at 26 hours, at which time there was only marginal proliferation in any of the cultures. At later time points CTLA-4/B7 blockade resulted in a 1½ to 2 fold increase in proliferation. The enhancing effect of this blockade was even more apparent at the level of IL-2 production. As shown in FIG. 8B, IL-2 was detectable, although at low levels, in anti-CD3/CD28 stimulated cultures by 26 hours. The addition of either anti-CTLA-4 Fab or CTLA-4lg resulted in an increase of about six fold in the amount of IL-2 accumulated by 26 hours, and nearly ten fold by 40 hours.

The kinetics of the inhibition of proliferation and IL-2 production were examined by crosslinking CTL-A4 together with CD3 and CD28 using anti-body coated microspheres. The kinetics of thymidine incorporation are shown in FIG. 8C. Significant incorporation was detectable by 26 hours in cultures stimulated by anti-CD3 and anti-CD28. There was essentially no incorporation detectable at 26 hours when CTLA-4 was also engaged, and proliferation was 3–4 fold lower in these cultures throughout the assay period. As shown in FIG. 8D, an even more pronounced inhibition of IL-2 production was observed. IL-2 was readily detectable in anti-CD3/CD28 stimulated cultures by 16 hours, and increased up to 40 hours. When CTLA-4 was also engaged, IL-2 was only barely detectable even after 30 hours, and reached a level of only about ⅕ of that in the control cultures at its peak at 42 hours.

These results indicate that the inhibitory effects of CTLA-4, whether mediated by its natural ligand or by antibody crosslinking, can be detected early in the course of activation and are not due to precipitous termination of responses at later stages in the process.

CTLA-4 Engagement Does Not Induce Cell Death, But Prevents Cell Cycle Progression. One mechanism which could account for the inhibition of proliferation by CTLA-4 would be the induction or enhancement of cell death. Since the inhibition was detectable throughout the culture period, the kinetics of cell death occurring in T cell cultures was assessed. Hematocytometric counting of cells stained with the vital dye trypan blue showed that the total recovery of cells from the cultures was essentially 100% of input, even in those in which proliferation did not occur. In unstimulated cultures, the number of non-viable cells increases over the culture period, reaching 50% after 54 hours. There was a slight increase in the number of dead cells recovered from cultures stimulated with anti-CD3 alone, especially at the earlier time points. Consistent with the proliferation data, cultures costimulated with anti-CD28 yielded an increase in viable cells after 42 hours, with a total yield of over 300% at 78 hours. Stimulation with anti-CD3 plus anti-CTLA-4 did not result in an increase in dead cells over that observed in unstimulated cultures or in cultures stimulated with anti-CD3 alone. There was also no increase in recovery of dead cells from cultures stimulated with anti-CTLA-4 in the presence of anti-CD3 and anti-CD28 over that of cultures stimulated by anti-CD3 and anti-CD28. Throughout the culture period the recovery of viable cells was in fact higher than that from unstimulated cultures or cultures stimulated with anti-CD3 alone. These data indicate that crosslinking of CTLA-4 does not induce cell death as detectable at the level of membrane permeability.

As a more direct and sensitive measure of cell death and cell cycle status, propidium iodide staining of permeabilized cells was used to measure DNA content at various stages in the cultures. Each culture was started with identical numbers of cells, and equal fractions of the cultures were analyzed in order to allow a comparison of the absolute number of recovered cells in the G0/G1, S/G2, and sub-diploid populations. The results are presented in FIGS. 9A to 9E. Total cell recovery was essentially 100% of input or higher under all 25 stimulation conditions. Greater than 99% of input cells were in $G_0/G_1$. In unstimulated cultures, the number of cells with sub diploid amounts of DNA indicative of apoptosis increased to slightly greater than 50% of the total over the course of the culture period. A similar pattern was observed in cultures stimulated with anti-CD3 alone, although slightly higher numbers of cells in $S/G_2$ were obtained. In cultures costimulated with anti-CD28, there was a significant increase in the number of cells in $S/G_2$ as early as 20 hours, and this number increased progressively over the assay period. The DNA profiles of cells stimulated with anti-CD3 together with anti-CTLA-4 were essentially the same as unstimulated or anti-CD3 stimulated cultures throughout the assay period with no significant differences in the number of apoptotic cells. However, there were significantly fewer cells in $S/G_2$ in cultures stimulated with anti-CD3 plus anti-CTLA-4 relative to stimulation with anti-CD3 alone. Cultures stimulated with anti-CTLA-4 and anti-CD3 plus anti-CD28 had similar numbers or even fewer cells in the sub diploid population than any of the other conditions throughout the culture period. Thus there is no evidence of induction of apoptotic cell death by anti-CTLA-4 crosslinking at any time during the course of activation. The main effect of crosslinking CTLA-4 on cells stimulated with anti-CD3 and anti-CD28 is an inhibition of the increase in total viable cells, especially those in $S/G_2$. Together, these results indicate that CTLA-4 engagement inhibits cell cycle progression, and an arrest of cells in $G/G_1$.

CTLA-4 Engagement Partially Inhibits Induction of IL-2 Receptor Alpha Chain Expression. Another hallmark of T cell activation is upregulation of expression of CD25, the IL-2 receptor alpha chain. Flow cytometry was used to assess the expression of CD25 on T cells under conditions of CD28 costimulation with and without concomitant CTLA-4 ligation. Stimulation of T cells with anti-CD3 alone resulted in the induction of expression of CD25 on about 60% of T cells within 24 hours. Costimulation with anti-CD28 increased this expression with respect to both the number of positive cells and the level of expression at 24 hours, and the expression was further enhanced at 60 hours of culture. When CTLA-4 was also engaged, CD25 expression was expressed by a smaller fraction of the cells (47% vs. 80%) and the mean level of expression was much lower at 24 hours (mean fluorescence index 162 vs. 194) and at 60 hours (MFI 332 vs. 669) relative to cultures costimulated with anti-CD28. This data demonstrate that CTLA-4 engagement inhibits the upregulation of CD25 throughout activation.

CTLA-4 Engagement Partially Inhibits Expression of the Early Activation Marker CD69. CD69 is a early and transient marker of T cell activation. A kinetic analysis of the effects of CD28 and CTLA4 engagement on induction of CD69 expression was performed. At 12 hours, CD69 was expressed by greater than 50% of T cells activated with CD3 alone or costimulted with anti-CD28, while fewer than 15% of costimulated cells also subjected to CTLA-4 ligation were positive. At 24 hours, CD69 expression was detectable, albeit in a heterogeneous pattern, on greater than 75% of CD28 costimulted cells. At this point fewer than 45% of cells from cultures in which CTLA-4 had also been engaged expressed CD69 and the level of expression was reduced. By 36 hours, CD69 expression had returned to essentially resting levels in all the cultures. CD28 costimulation augments and prolongs CD69 expression, whereas CTLA-4 ligation inhibits the initial upregulation of CD69. This result is consistent with the observation that CD69 levels were found to be constitutively elevated on T cells isolated from CTLA-4 deficient mice and provides additional evidence suggesting a role for CTLA-4 in preventing the early induction of T cell activation.

These data demonstrate that CTLA-4 mediates inhibition of proliferation and IL-2 production by resting T cells in the absence of CTLA-4 mediated cell death. The recovery of viable and non-viable cells from anti-CTLA-4 inhibited cultures is similar to that observed in control antibody or anti-CD3 stimulated cultures. There is no accumulation of cells with sub-diploid quantities of DNA associated with apoptotic cell death even 1-2 days after inhibitory effects of CTLA-4 crosslinking are first observed at the level of proliferation and IL-2 production. Finally, CTLA-4 crosslinking arrests T cells in a G0/G1 phase of the cell cycle. Taken together, these data clearly demonstrate that inhibition of T cell proliferation and IL-2 secretion by CTLA-4 can occur in the absence of cell death. An important implication of the data presented here is that CTLA-4 may have a role in regulating T cell responses at early stages in the process. Our data do not reveal a precipitous termination of ongoing responses, but rather an inhibition and delay of events associated with the progression of T cell activation.

The above results demonstrate that the subject treatment with CTLA-4 blocking agents increases the response of T cells to antigenic stimulation. The growth of tumor cells in vivo is greatly diminished in the presence of the subject blocking agents. The effects are observed against unmanipulated, wild-type tumors. CTLA-4 blocking agents not only represent a novel approach to tumor therapy, but, by removing potentially competing inhibitory signals, may be a particularly useful adjunct to other therapeutic approaches involving the co-stimulatory pathway. Class switching by immunoglobulin producing cells, a measure of T cell help, is greatly increased. The cell response to immunization with peptide antigens is also greatly increased by the treatment with the subject agents.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of decreasing the growth of non-T cell tumor cells in a host, the method comprising:

administering to said host an effective dose of a CTLA-4 blocking agent, wherein said blocking agent is capable of specifically binding to the extracellular domain of CTLA-4 and inhibiting CTLA-4 signaling;

wherein said dose is effective to decrease the growth of said tumor cells.

2. A method according to claim 1, wherein said CTLA-4 blocking agent is an oligopeptide.

3. A method according to claim 2, wherein said oligopeptide is an antibody or fragment thereof.

4. A method according to claim 3, wherein said antibody is a monoclonal antibody.

5. A method according to claim 1, wherein said administration is by intravenous injection.

6. A method according to claim 1, further comprising adminstering to said host a cytokine that stimulates antigen presenting cells.

7. A method according to claim 6, wherein said cytokine is at least one of IL-3, GM-CSF, G-CSF, M-CSF and IL-12.

8. A method according to claim 1, further comprising administering to said host at least one tumor cell antigen.

9. A method according to claim 1, wherein said tumor cells are carcinoma cells.

10. A method according to claim 1, wherein said tumor cells are fibrosarcoma cells.

11. A method of decreasing the growth of carcinoma cells in a host, the method comprising:

administering intravenously to said host an effective dose of a CTLA-4 blocking agent, wherein said blocking agent is an antibody capable of specifically binding to the extracellular domain of CTLA-4 and inhibiting CTLA-4 signaling;

wherein said dose is effective to decrease the growth of said carcinoma cells.

* * * * *

UNITED STATES PATENT AND TRADEMARK OFFICE
CERTIFICATE OF CORRECTION

PATENT NO. : 5,811,097
DATED : September 22, 1998
INVENTOR(S) : ALLISON et al.

It is certified that error appears in the above-indentified patent and that said Letters Patent is hereby corrected as shown below:

Column 2, lines 14 and 15, delete "CTLA-41g" and insert therefore --CTLA-4Ig--.

Column 6, line 55, delete "sIg" and insert therefore -- sIg--.

Column 9, line 18, delete "larynx, cavity" and insert therefore --larynx.--

Column 9, line 19, delete "tongue, larynx,".

Column 9, line 44, delete --"HMB45" and insert therefore --HMB-45--.

Column 12, lines 23 and 24, delete "TATACTTACCAGMTCCG" and insert therefore -- TATACTTACCAGAATCCG--.

Column 13, line 4, delete "CTLA4Ig" and insert therefore --CTLA4Ig--.

Column 13, line 25, delete "CTLA-4Ig" and insert therefore --CTLA-4Ig--.

Column 13, line 30, delete "CTLA-4Ig" and insert therefore --CTLA-4Ig--.

Column 13, line 37, delete "CTLA-4Ig" and insert therefore --CTLA-4Ig--.

Column 13, line 41, delete "CTLA-4Ig" and insert therefore --CTLA-4Ig--.

Column 13, line 51, delete "CTLA4Ig" and insert therefore --CTLA4Ig--.

Column 13, line 52, delete "CTLA4Ig" and insert therefore --CTLA4Ig--.

UNITED STATES PATENT AND TRADEMARK OFFICE
CERTIFICATE OF CORRECTION

PATENT NO.  : 5,811,097
DATED       : September 22, 1998
INVENTOR(S) : ALLISON et al.

It is certified that error appears in the above-indentified patent and that said Letters Patent is hereby corrected as shown below:

Column 13, line 54, delete "4lg binding" and insert therefore --4Ig binding--.

Column 13, line 54, delete "CTLA4lg" and insert therefore --CTLA4Ig--.

Column 13, line 55, delete "CD4lg" and insert therefore --CD4Ig--.

Column 13, line 58, delete "CD4lg" and insert therefore --CD4Ig--.

Column 13, line 61, delete "CD4lg" and insert therefore --CD4Ig--.

Column 13, line 62, delete "CD4lg" and insert therefore --CD4Ig--.

Column 13, line 65, delete "CTLA-4lg)" and insert therefore --CTLA-4Ig)--.

Column 14, line 32, delete "CTLA-4lg" and insert therefore --CTLA-4Ig--.

Column 14, line 34, delete "4lg" and insert therefore --4Ig--.

Column 15, line 30, delete "CTLA4lg" and insert therefore --CTLA-4Ig--.

Column 15, line 30, delete "CD4lg" and insert therefore --CD4Ig--.

Column 15, line 38, delete "CTLA-4lg" and insert therefore --CTLA-4Ig--.

Column 15, line 38, delete "CD4lg" and insert therefore --CD4Ig--.

Column 15, line 39, delete "CTLA-4lg" and insert therefore --CTLA-4Ig--.

Column 15, line 43, delete "CTLA-4lg" and insert therefore --CTLA-4Ig--.

UNITED STATES PATENT AND TRADEMARK OFFICE
CERTIFICATE OF CORRECTION

PATENT NO. : 5,811,097
DATED : September 22, 1998
INVENTOR(S) : ALLISON et al.

It is certified that error appears in the above-indentified patent and that said Letters Patent is hereby corrected as shown below:

Column 15, line 46, delete "CTLA-41g" and insert therefore --CTLA-4Ig--.

Column 16, line 17, delete "1g" and insert therefore --Ig--.

Column 17, line 24, delete "S40" and insert therefore --SV40--.

Column 21, line 35, delete "CTLA41g" and insert therefore --CTLA4Ig--.

Column 21, line 50, delete "CTLA41g" and insert therefore --CTLA4Ig--.

Column 21, line 55, delete "CTLA-41g" and insert therefore --CTLA-4Ig--.

Column 21, line 62, delete "CTLA-41g" and insert therefore --CTLA-4Ig--.

Column 21, line 64, delete "CTLA-41g" and insert therefore --CTLA-4Ig--.

Column 21, line 65, delete "CTLA-41g" and insert therefore --CTLA-4Ig--.

Column 22, line 2, delete "CTLA-41g" and insert therefore --CTLA-4Ig--.

Column 23, line 32, delete "1 1g/ml" and insert therefore --1Ig/ml--.

Column 24, line 53, delete "Lysis ll" and insert therefore --Lysis II--.

Column 27, line 29, delete "CTLA-41g" and insert therefore --CTLA4Ig--.

Column 27, line 50, delete "50" and insert therefore --50 $\mu$l--.

UNITED STATES PATENT AND TRADEMARK OFFICE
CERTIFICATE OF CORRECTION

PATENT NO. : 5,811,097
DATED : September 22, 1998
INVENTOR(S) : ALLISON et al.

It is certified that error appears in the above-indentified patent and that said Letters Patent is hereby corrected as shown below:

Column 27, line 57, delete "CTLA-41g" and insert therefore --CTLA-4Ig--.

Column 28, line 59, delete "JES-6-1A12" and insert therefore --JES6-1A12--.

Column 29, line 16, delete "CTLA-41g" and insert therefore --CTLA-4Ig--.

Column 29, line 18, after "increase" and before "proliferation", insert --in--.

Column 29, line 26, delete "CTLA-41g" and insert therefore --CTLA-4Ig--.

Column 29, line 31, delete "anti-body" and insert therefore --antibody--.

Column 30, line 20, delete "25".

Column 30, line 47, delete "G/G$_1$" and insert therefore G$_0$/G$_1$ --.

Column 32, line 19, after "The" and before "cell" insert --T--.

Signed and Sealed this

Twenty-fourth Day of October, 2000

Attest:

Q. TODD DICKINSON

*Attesting Officer*   *Director of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:1:

```
TTACTCTACT CCCTGAGGAG CTCAGCACAT TTGCC                                    35
```

( 2 ) INFORMATION FOR SEQ ID NO:2:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:2:

```
TATACTTACC AGAATCCGGG CATGGTTCTG GATCA                                    35
```